United States Patent
Taniguchi et al.

(10) Patent No.: US 9,151,719 B2
(45) Date of Patent: Oct. 6, 2015

(54) INSPECTION APPARATUS

(71) Applicant: Hitachi High-Technologies Corporation, Minato-ku, Tokyo (JP)

(72) Inventors: Koichi Taniguchi, Tokyo (JP); Kei Shimura, Tokyo (JP); Sachio Uto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/361,657

(22) PCT Filed: Nov. 19, 2012

(86) PCT No.: PCT/JP2012/079886
§ 371 (c)(1),
(2) Date: May 29, 2014

(87) PCT Pub. No.: WO2013/099468
PCT Pub. Date: Jul. 4, 2013

(65) Prior Publication Data
US 2014/0333923 A1 Nov. 13, 2014

(30) Foreign Application Priority Data
Dec. 27, 2011 (JP) ................................. 2011-284707

(51) Int. Cl.
*G01N 21/00* (2006.01)
*G01N 21/95* (2006.01)
*G01N 21/956* (2006.01)
*G02B 26/06* (2006.01)
*G02B 26/08* (2006.01)
*G01N 21/47* (2006.01)

(52) U.S. Cl.
CPC ...... *G01N 21/9505* (2013.01); *G01N 21/95684* (2013.01); *G01N 21/47* (2013.01); *G01N 21/4788* (2013.01); *G01N 2021/4707* (2013.01); *G02B 26/06* (2013.01); *G02B 26/0825* (2013.01)

(58) Field of Classification Search
USPC ....................... 356/237.1–237.6, 239.1–239.8
See application file for complete search history.

(56) References Cited

U.S. PATENT DOCUMENTS

| | | | |
|---|---|---|---|
| 6,608,676 B1 | 8/2003 | Zhao et al. | |
| 7,098,055 B2 | 8/2006 | Noguchi et al. | |
| 7,535,561 B2 | 5/2009 | Chikamatsu et al. | |
| 2004/0100629 A1 | 5/2004 | Stokowski et al. | |
| 2006/0203231 A1 | 9/2006 | Uto et al. | |
| 2009/0059216 A1 | 3/2009 | Shibata et al. | |
| 2012/0092657 A1* | 4/2012 | Shibata et al. | ............. 356/237.4 |

FOREIGN PATENT DOCUMENTS

| | | |
|---|---|---|
| JP | 04-350613 A | 12/1992 |
| JP | 08-304732 A | 11/1996 |

(Continued)

*Primary Examiner* — Tri T Ton
(74) *Attorney, Agent, or Firm* — Miles & Stockbridge P.C.

(57) ABSTRACT

When it is tried to detect a microscopic defect, it is desired that the width of the above-mentioned illuminated region in the minor axis direction should be short. In the related art, although an illuminated region is formed by converging light by some means, it is not easy to form an illuminated region with a narrower width. This is because various aberrations possessed by optical elements themselves used for convergence, aberrations possessed by other optical elements disposed on optical paths, assembly errors, and the like have undesired influence on the formation of linear illumination. In the related art, sufficient consideration has not been paid to the above points. The present invention is characterized in that it includes a system for changing the wavefront of light.

13 Claims, 18 Drawing Sheets

DEFORMABLE MIRROR 309

ACTUATOR 3092

(56) References Cited

FOREIGN PATENT DOCUMENTS

| JP | 2006-250739 A | 9/2006 |
| JP | 2008-058111 A | 3/2008 |
| JP | 2011-053186 A | 3/2011 |
| JP | 2011-069769 A | 4/2011 |
| JP | 2011-154039 A | 8/2011 |

* cited by examiner

FIG.3
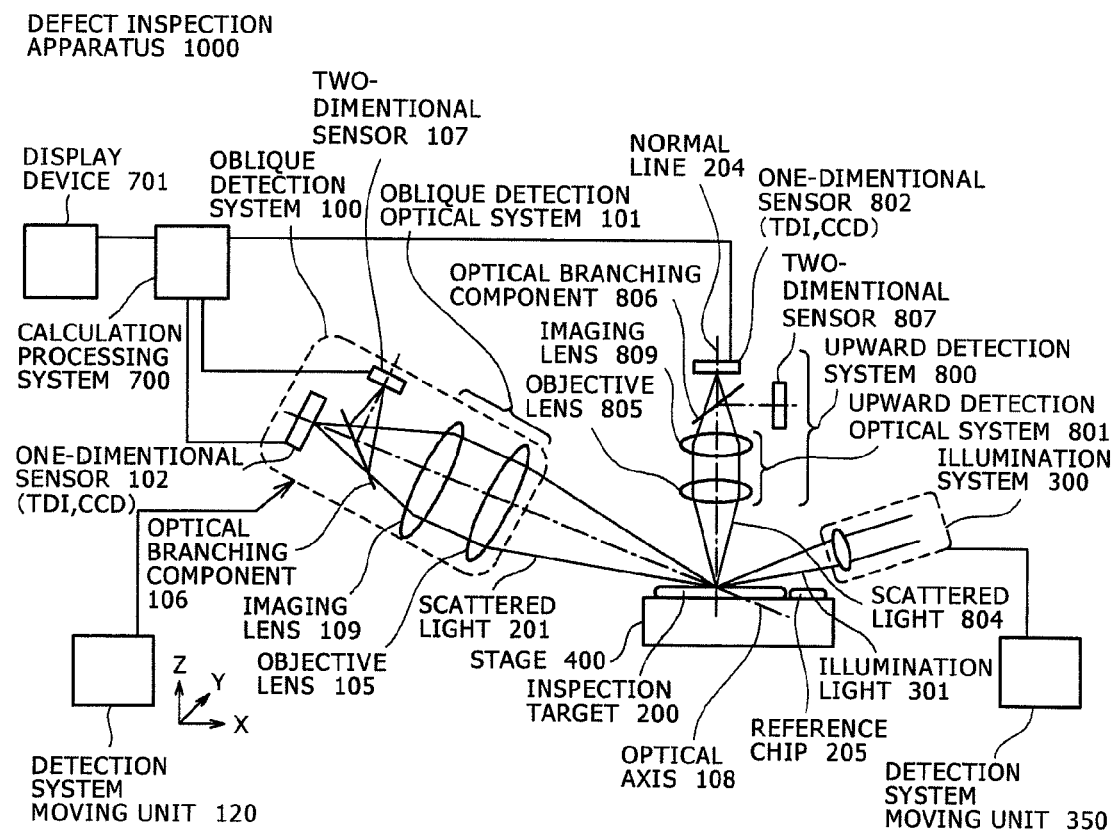
(a)
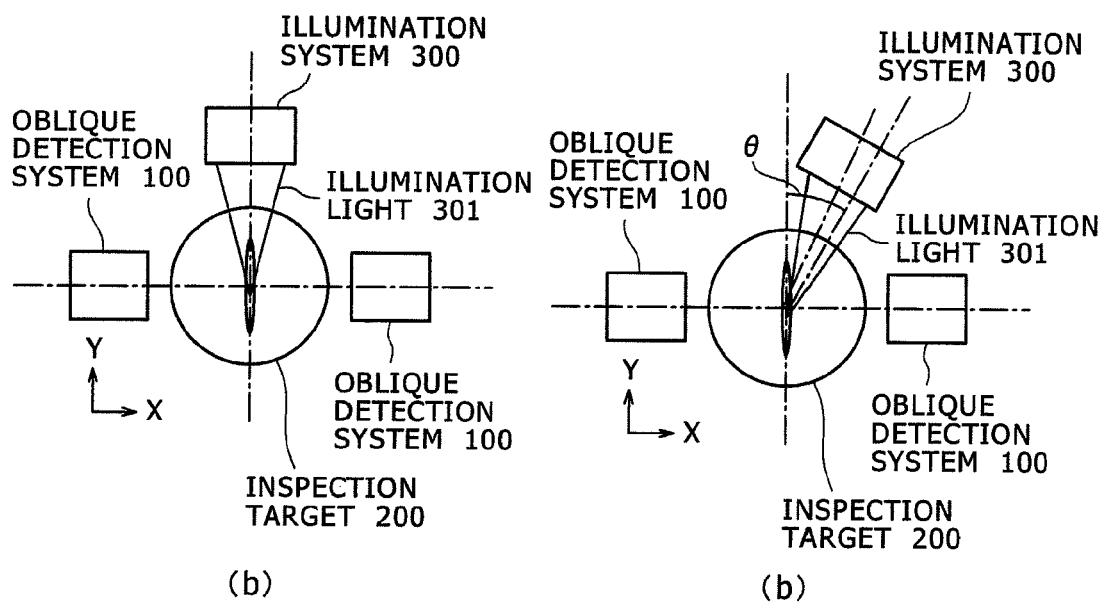
(b)  (b)

FIG. 6
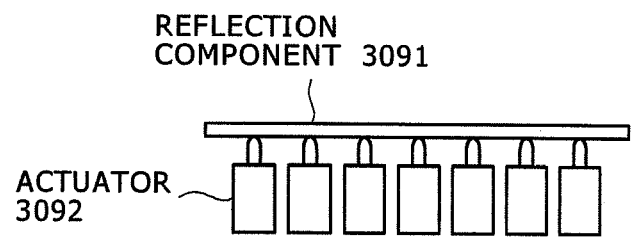
FIG. 7
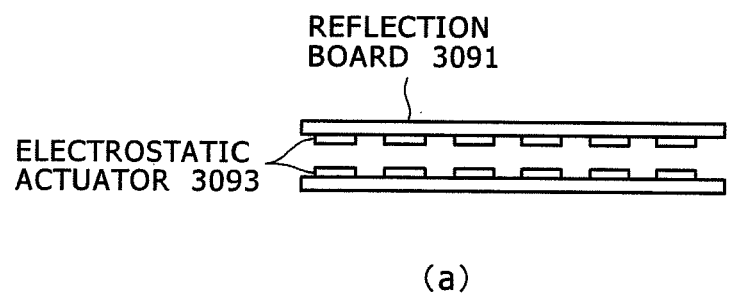
(a)
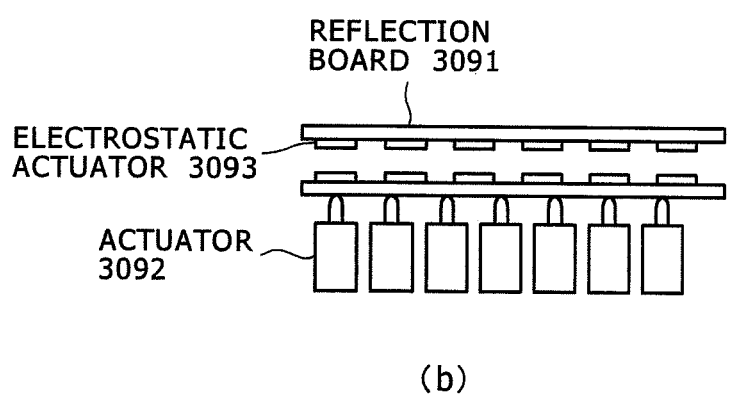
(b)

FIG. 8
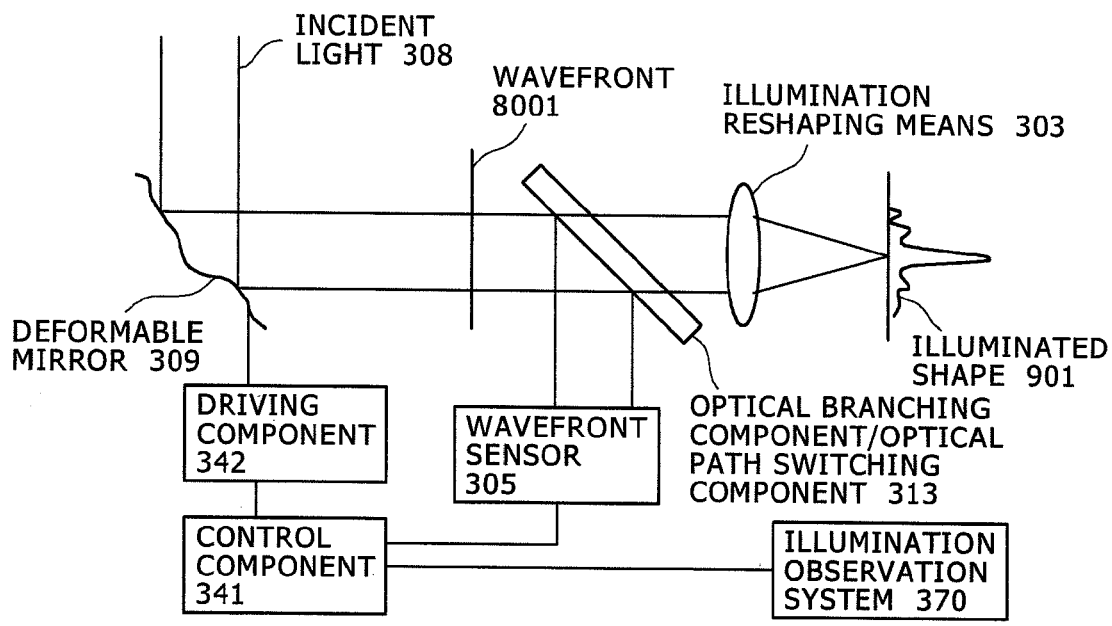
(a)
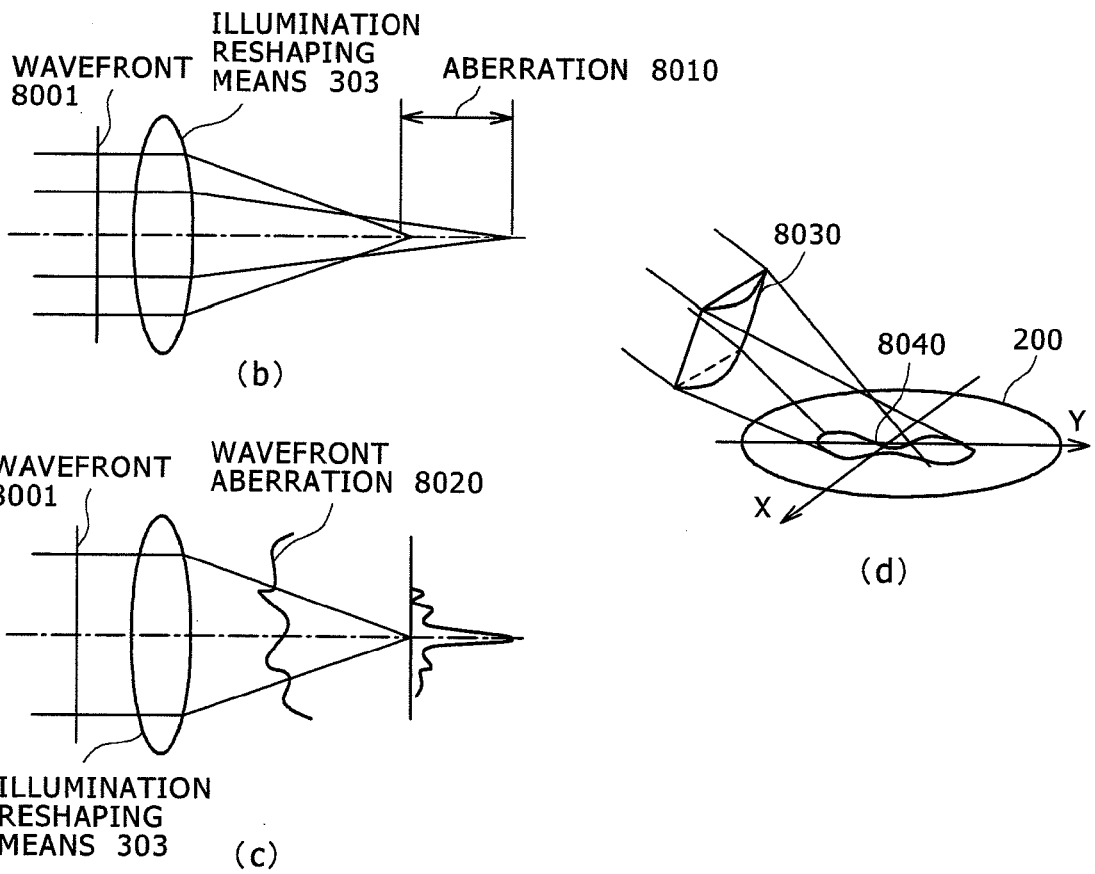
(b)
(c)
(d)

FIG.10
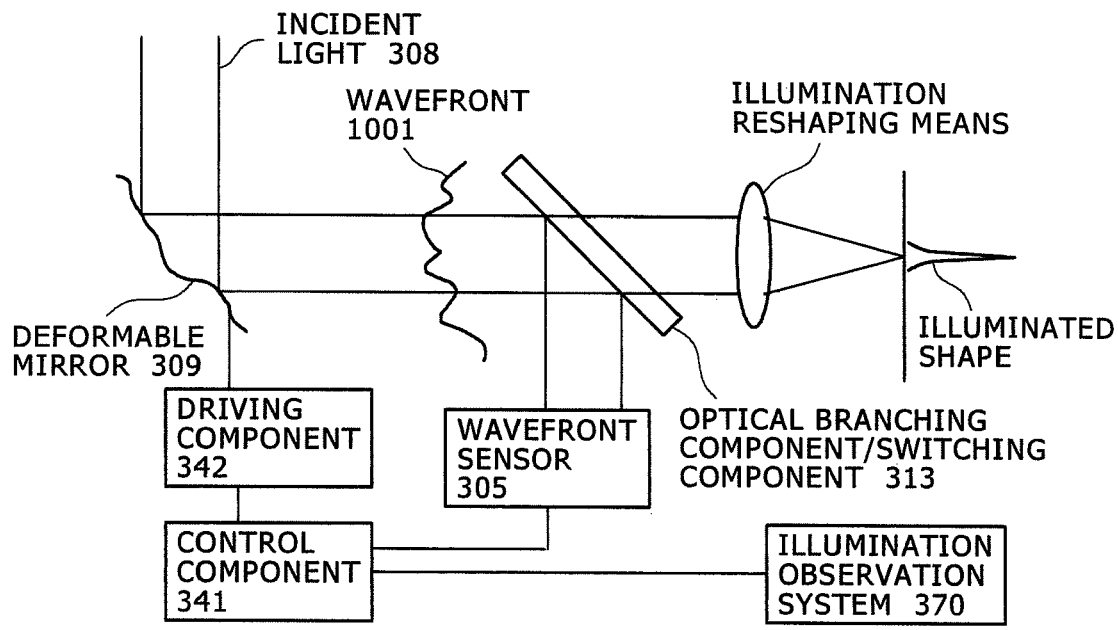
(a)
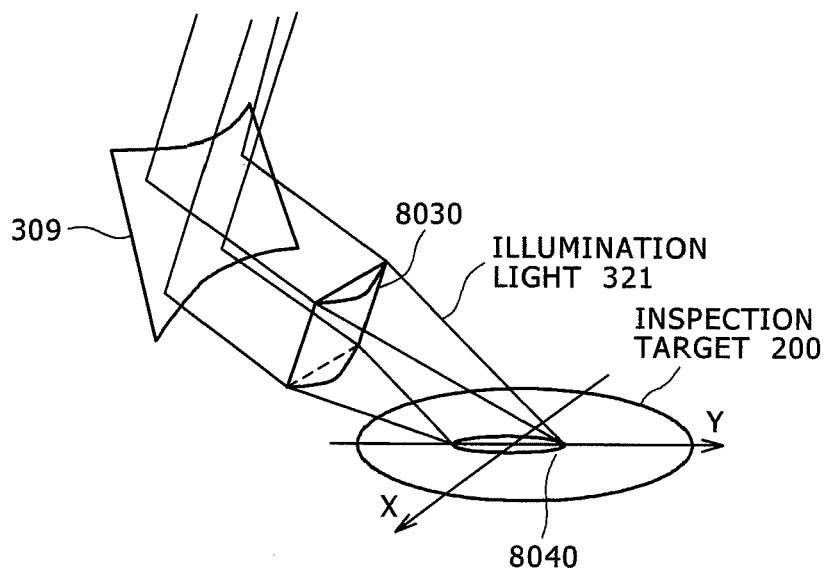
(b)

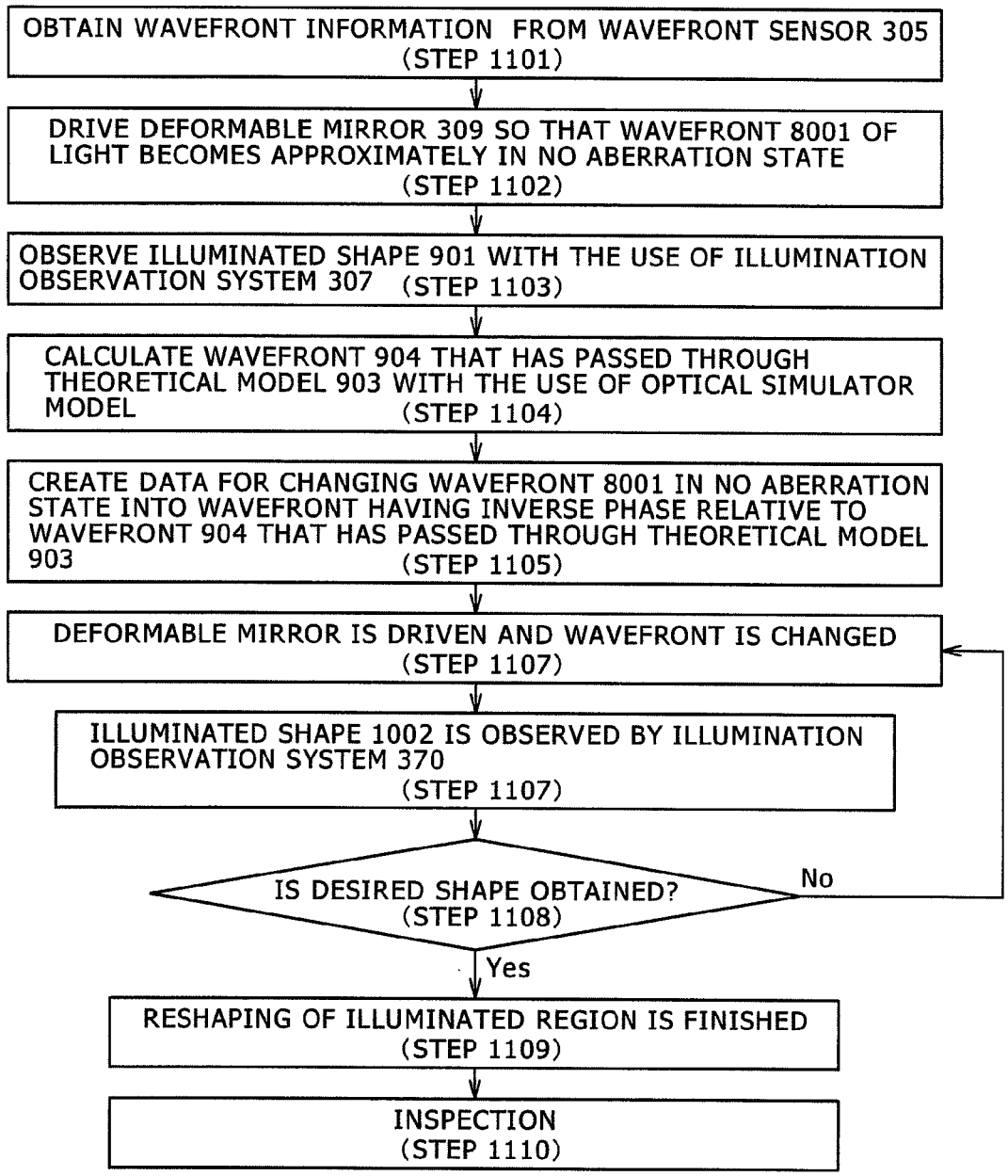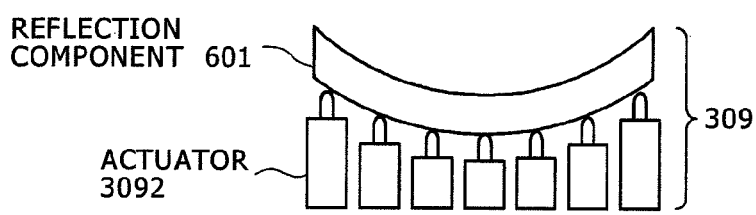

FIG.22
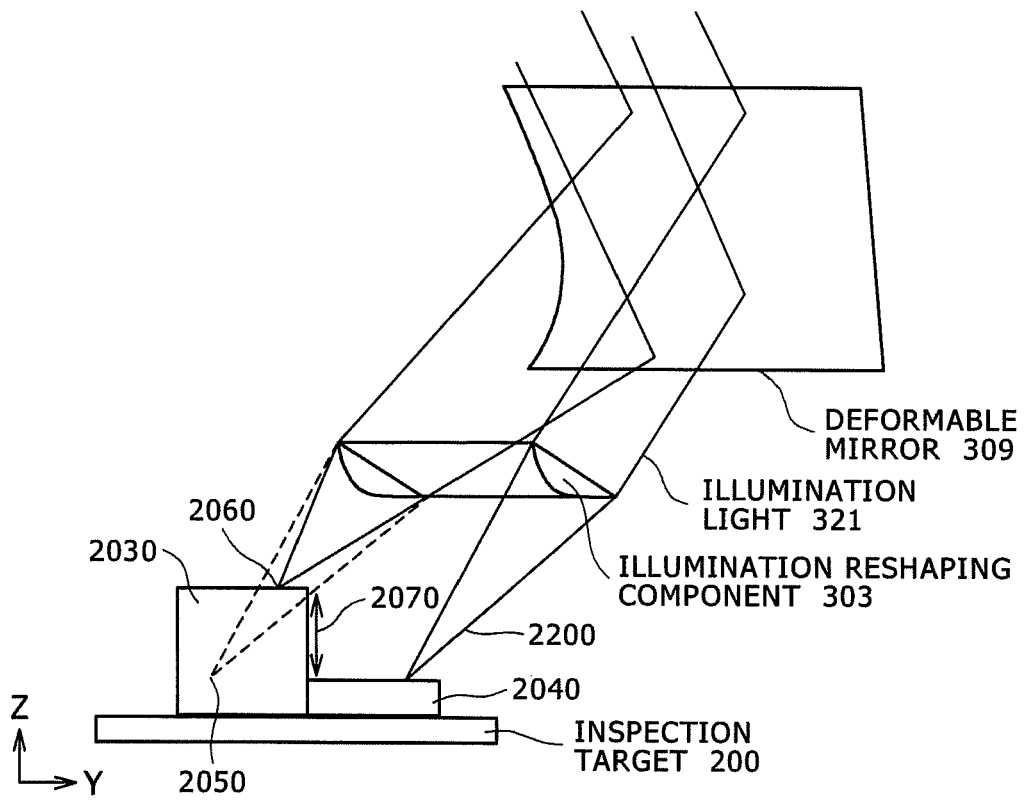
(a)
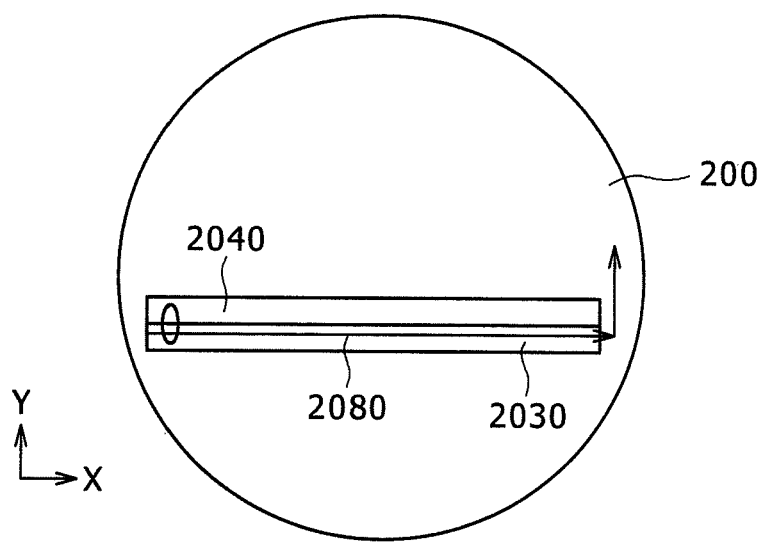
(b)

INSPECTION APPARATUS

TECHNICAL FIELD

The present invention relates to an inspection apparatus that inspect defects on a substrate.

BACKGROUND ART

In semiconductor processes, foreign substances (also referred to as defects in the broad sense of the term) on the surface of a semiconductor substrate (wafer) cause insulation failures and short circuits between wirings, and also cause insulation failures of capacitors and breakages of oxide films, and the like. The foreign substances includes substances such as created from moving parts of a carrier, device, created from human bodies, created in chemical reactions in processing devices in which process gases are used, and mixed in medicals and materials. Then these foreign substances are attached to the surface of the wafer for various reasons. In addition, in the manufacturing process of a liquid crystal display element, if a foreign substance gets mixed in a pattern of the display element, this liquid crystal display element can not be used as a display element. Further, the same can be said for the case of the manufacturing process of a printed-circuit board, and the contamination with foreign substances leads to short circuits and contact failures between patterns. Therefore, in order to manage the process yield, it becomes important to detect foreign substances on substrates such as a wafer and feed back the information to the manufacturing process.

Apparatuses that are used for detecting foreign substances and the like on the above-mentioned substrates are so-called inspection apparatuses. The inspection apparatuses can be roughly classified into two types: one type is a surface inspection apparatus for inspecting mirror surface wafers, and the other type is a wafer-with-patterns inspection apparatus for inspecting wafers on which circuit patters are formed. In particular, Patent Literature 1, Patent Literature 2, and Patent Literature 3 are well known as wafer-with-patterns inspection apparatus for inspecting wafers on which circuit patters are formed. In Patent Literatures 1 to 3, an illuminated region having a two-dimensional spread in the major axis direction and the minor axis direction is formed on a substrate. Patent Literature 4 and Patent Literature 4 are well known for disclosing the related art regarding another inspection apparatus. In addition, Patent Literature 6 is well known for disclosing a technology for illuminating a substrate. Patent Literature 7 and Patent Literature 8 are well known for disclosing other technologies.

CITATION LIST

Patent Literature

Patent Literature 1: U.S. Pat. No. 7,098,055
Patent Literature 2: U.S. Pat. No. 6,608,676
Patent Literature 3: United States Patent Application Publication No. 2009/0059216
Patent Literature 4: Japanese Unexamined Patent Application Publication No. 2011-69769.
Patent Literature 5: Japanese Unexamined Patent Application Publication No. 2008-58111
Patent Literature 6: Japanese Unexamined Patent Application Publication No. Hei8 (1996)-304732
Patent Literature 7: U.S. Pat. No. 7,535,561
Patent Literature 8: Japanese Unexamined Patent Application Publication No. Hei4 (1992)-350613

SUMMARY OF INVENTION

Technical Problem

When it is tried to detect a microscopic defect, it is desired that the width of the above-mentioned illuminated region in the minor axis direction should be short. In the related art, although an illuminated region is formed by converging light by some means, it is not easy to form an illuminated region with a narrower width. This is because an aberration that cannot be removed for some design reason, a wavefront aberration owing to the processing accuracies of optical elements themselves that are used for convergence, and the like have undesired influence on the formation of linear illumination. In the related art, sufficient consideration has not been paid to the above point.

Solution to Problem

The present invention is characterized in that it includes a system for changing the wavefront of light.

Advantageous Effects of Invention

According to the present invention, a more highly sensitive inspection can be performed than the inspection according to the related art.

BRIEF DESCRIPTION OF DRAWINGS

FIG. 3 is a schematic block diagram showing a defect inspection apparatus according to a first embodiment.

FIG. 6 is a cross-section view of the deformable mirror 309.

FIG. 7 is a diagram for explaining a deformable mirror including electrostatic actuators.

FIG. 8 is a diagram for explaining a procedure of illumination reshaping (No. 1).

FIG. 10 is a diagram for explaining the procedure of illumination reshaping (No. 3)

FIG. 11 is a flowchart for explaining the procedure of illumination reshaping.

FIG. 12 is a diagram for explaining a second embodiment.

FIG. 22 is a diagram for explaining the tenth embodiment (No. 3).

DESCRIPTION OF EMBODIMENTS

Embodiments of the present invention will be described with reference to the accompanying drawings hereinafter.

First Embodiment

Figure 1:
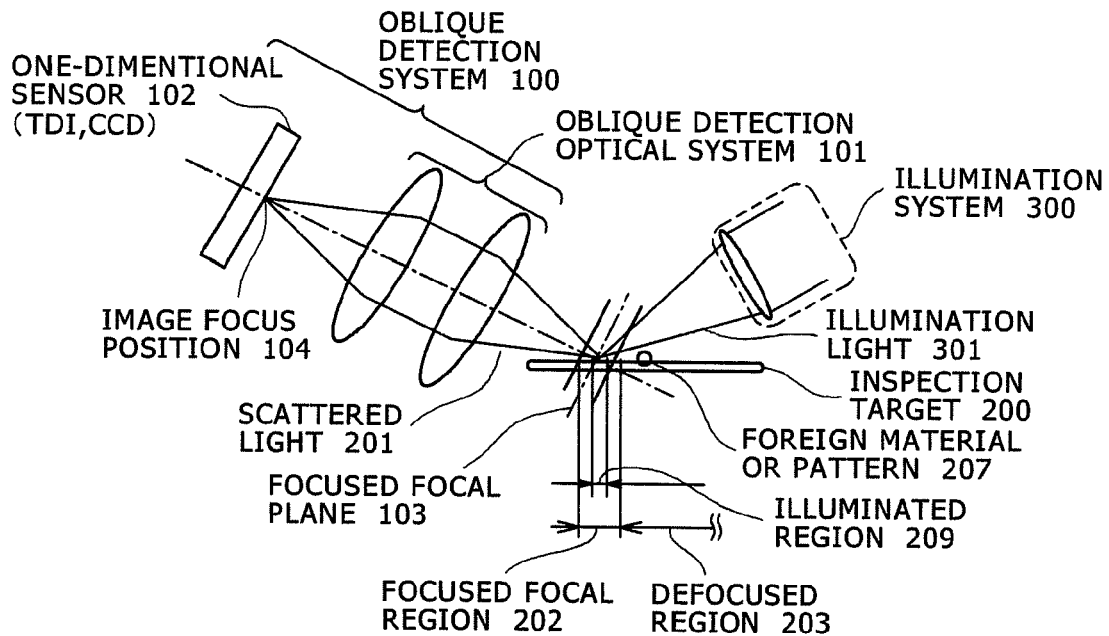
FIG. 1 is a diagram for explaining a reason why an illumination width narrower than the focal depth of an oblique detection system is required.
Figure 2:
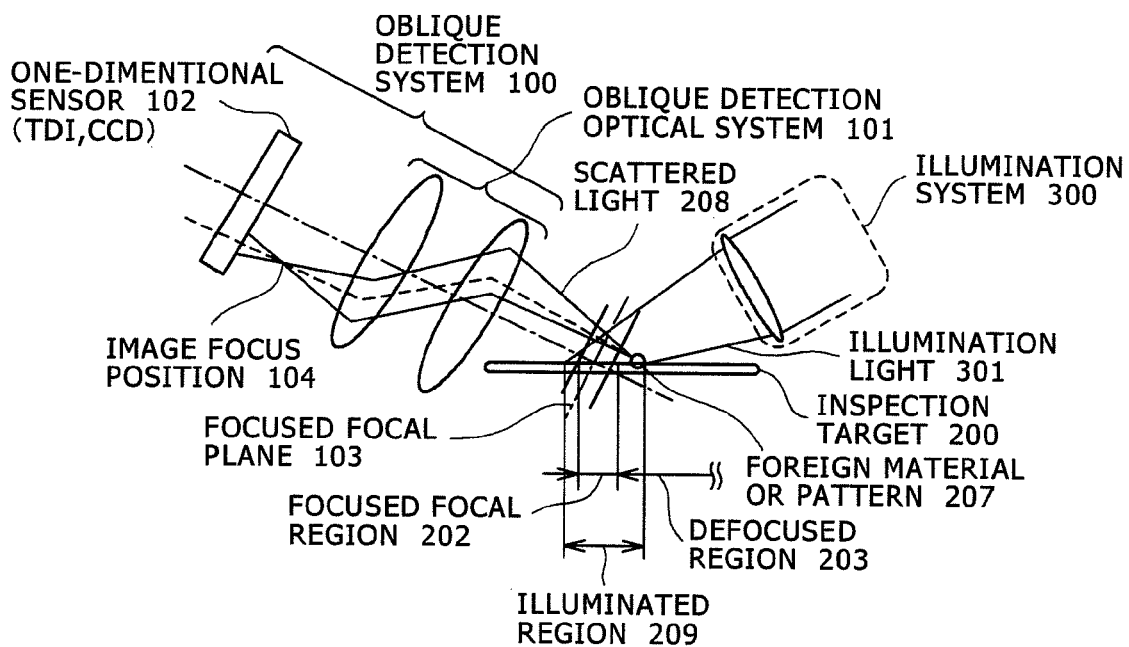
FIG. 2 is a diagram for explaining the reason why an illumination width narrower than the focal depth of an oblique detection system is required (continued from FIG. 1).

At the beginning the explanation of a first embodiment, the reason why an illuminated region with a narrow width in the minor axis direction is required will be explained first. FIG. 1 and FIG. 2 show the reason why an illumination width narrower than the focal depth of an oblique detection system is required when the oblique detection system is used in a defect inspection apparatus.

FIG. 1 is a diagram showing a normal image focus relationship in the case where a later-mentioned illuminated region 209 is reshaped so as to have its width equal to or narrower than the after-mentioned focused focal region 202 in an inspection apparatus using an oblique detection system 100. A focused focal plane 103 shows a region that is included by the focused focal plane and the focal depth at the object side of the oblique detection system 100. The focused focal region 202 is a region where the focused focal plane 103 and the surface of an inspection target 200 intersect with each other. In FIG. 1, illumination light 301 emitted from an illumination system 300 is reshaped into linear light with its width equal to or narrower than the focused focal region 202, and the reshaped illumination light is irradiated onto the focused focal region 202. In this case, because the reshaped illumination light does not illuminate a defocused region 203, only scattered light 201 from the focused focal region 202 is created, the scattered light is focused into an image by an oblique detection optical system 101 including an objective lens, a spatial filter, an imaging lens, and the like. The image built up in an image focus position 104 is received by the surface of a one-dimensional sensor 102. In this state, a focused image can be obtained by scanning the inspection target 200.

FIG. 2 is a diagram showing an image focus relationship in the case where the illuminated region 209 is wider than the focused focal region 202 in the inspection apparatus using the oblique detection system 100. In FIG. 2, the illumination light 301 emitted from the illumination system 300 forms the illuminated region 209 on the inspection target 200. In FIG. 2, in the case where the illuminated region 209 is larger than the focused focal region 202, the defocused region 203 is also illuminated. In this case, not only the scattered light 201 created from the focused focal region 202, but also scattered light 208 created from a foreign substance or a pattern 207 existing on the defocused region 203 is received in a defocused state by the one-dimensional sensor 102, which leads to the degradation of the detected image.

The above is the reason why it is desired that linear illumination with its width equal to or narrower than the focused focal region 202 should be used in the case where the oblique detection system 100 is used.

Next, a defect inspection apparatus according to this embodiment will be explained below. FIG. 3(a) is a schematic block diagram of the defect inspection apparatus according to this embodiment. In FIG. 3(a), a defect inspection apparatus 1000 includes: an illumination system 300; an oblique detection system 100; an upward detection system 800; a stage 400 on which an inspection target 200 is disposed to be scanned by illumination light; a one-dimensional sensor 102 (a time delay integration sensor (TDI sensor), a charge-coupled device, or the like); a one-dimensional sensor 802; a calculation processing system 700 that processes images obtained by the one-dimensional sensors 102 and 802 in order to detect defects; a two-dimensional sensor 107; a two-dimensional sensor 807; a display device 701 for displaying images obtained by the two-dimensional sensors 107 and 807; an optical branching component 106; and a reference chip 205 (a chip in which standard circuit patterns are formed) that is used for detecting the focused focal position of the oblique detection system 100. The reference chip 205 is disposed on the stage 400. In addition, as the reference chip, standard particles that are polystyrene latex balls attached onto a mirror surface substrate can be used.

The calculation processing system 700 processes the image 500 of the reference chip 205 obtained by the two-dimensional sensor 107, detects the focused focal recognition position 502 of the oblique detection system 100, and controls the stage 400 and the illumination system 300. In an actual inspection, the calculation processing system 700 compares the image of a chip (an image to be inspected) on the inspection target 200 obtained from at least one of the oblique detection system 100 and the upward detection system 800 with the reference image (the image of chips lying next to the chip whose image is to be inspected) on the inspection target 200, and performs threshold processing on the comparison result in order to find a defect on the inspection target 200. This defect detection operation is performed in synchronization with the scanning operation in x and y directions performed by the stage 400. The comparison of an inspection image with a reference image and threshold processing are performed in the units of the so-called dies or in the units of the so-called cells. In addition, if an inspection apparatus includes plural optical detection systems as is the case with this embodiment, there is a case where the comparison of an inspection image with a reference image and threshold processing are performed in the units of optical detection systems in the inspection apparatus. Further, there is a case where, after the comparison and the threshold processing are performed in units of the detection systems, defect detection is performed using the so-called characteristic quantities, that is, the defect detection is performed by integrally processing the characteristic quantities. These processes may be performed by a processing system separately installed instead of the calculation processing system 700. The control over the stage 400 and the illumination system 300 may also be performed by a control unit separately installed.

The coordinate system of the defect inspection apparatus 1000 is defined so that the direction of the z-axis is the direction of the normal line 204 of the upper surface of the inspection target 200, the direction of the x-axis is the direction of the scanning of the inspection target 200, and the direction of the y-axis is perpendicular to both directions of the x-axis and z-axis.

The stage 400 is configured to be movable in four directions, that is, the directions of the x-axis, y-axis, z-axis, and θ-axis.

The oblique detection system 100 includes: a detection optical system 101 having an objective lens 105 and an imaging lens 109; the one-dimensional sensor (a TDI sensor or a one-dimensional CCD sensor) 102; the optical branching component 106; and the two-dimensional sensor 107. The oblique detection system 100 mainly detects scattered light 201 that scatters in the oblique direction relative to the normal line 204.

If the one-dimensional sensor 102 is a TDI sensor and is capable of taking an image in the same way as a two-dimensional sensor does, the optical branching component 106 and the two-dimensional sensor 107 can be omitted. In addition, a spatial filter can be inserted on a Fourier transform plane formed between the objective lens 15 and the imaging lens 109 in order to shield diffracted light arriving from a repeated pattern of the inspection target 200 and remove the repeated pattern.

The one-dimensional sensor 102 is disposed in such a way that the longitudinal direction (which is perpendicular to the scanning direction) of the sensor is set approximately parallel with a direction that is the same direction in which the y-axis of the inspection target is projected by the oblique detection optical system 101. In addition, the light-receiving surface of the one-dimensional sensor 102 is disposed approximately perpendicular to the optical axis 108 of the oblique detection system 100.

A detection system moving unit 120 can move the oblique detection system 100.

The upward detection system 800 includes: an upward detection optical system 801 having an objective lens 805 and an imaging lens 809; the one-dimensional sensor (a TDI sensor or a one-dimensional CCD sensor) 802; an optical branching component 806; and the two-dimensional sensor 807. The upward detection system 800 detects scattered light that scatters in the direction of the normal line 204. If the one-dimensional sensor 802 is a TDI sensor and is capable of taking an image in the same way as a two-dimensional sensor does, the optical branching component 806 and the two-dimensional sensor 807 can be omitted. In addition, a spatial filter may be inserted on a Fourier transform plane formed between the objective lens 805 and the imaging lens 809 in order to shield diffracted light arriving from a repeated pattern of the inspection target 200 and remove the repeated pattern.

When the focused focal position of the oblique detection system 100 is detected, the reference chip 205 is disposed in the inspection position, and while an inspection operation is performed, the reference chip 205 is evacuatedly disposed in a position so that the reference chip 205 disposed there does not disturb the inspection operation. For example, the reference chip 205 is installed on the same horizontal plane as the inspection target 200 is installed relative to the stage 400, and when the focused focal position of the oblique detection system 100 is detected, the reference chip 205 is moved to a predefined position by moving the stage 400. In addition, the reference chip 205 is disposed within the visual field of an illumination observation system 370, which will be described later, when an illuminated shape 901 is observed.

As the optical branching component 106, a half mirror or a prism can be used. Alternatively, a mirror, which is taken into or taken out from an optical path in order to switch the optical path and lead the scattered light 201 to the two-dimensional sensor 107 at the time when the focused focal position is detected, can be used as the optical branching component 106. Similarly, as the optical branching component 806, a half mirror or a prism can be used. Alternatively, a mirror, which is taken into or taken out of an optical path in order to switch the optical path and lead the scattered light to the two-dimensional sensor 807 at the time when the inspection target 200 or the reference chip 205 is observed, and when the illumination light 301 is observed, may be used as the optical branching component 806.

In this embodiment, the illumination system 300 that illuminates the inspection target 200 is moved relative to the inspection target 200 by an illumination system moving unit 350.

Here, several variations can be thought of about the relationship among the illumination system 300, the inspection target 200, and the oblique detection system 100. One variation is shown in FIG. 3(b). In FIG. 3(b), the illumination system 300 converges the illumination light 301 in the y scanning direction of the stage 400, and forms a linear illuminated region on the inspection target 200. In this case, the longitudinal direction of the illuminated region coincides with the y scanning direction of the stage 400. In addition, in the case of FIG. 3(b), two oblique detection optical systems 100 are disposed, and these two oblique detection optical systems 100 are symmetrically disposed about the y scanning direction of the stage 400, and these oblique detection optical systems 100 are also symmetrically disposed about an incident plane determined by the normal line of the inspection target 200 and the optical axis of incident light. Another variation is shown in FIG. 3(c). In FIG. 3(c), the illumination system 300 converges the illumination 301 light in such a direction that an angle between a projected line obtained by projecting the optical axis of light radiated from the illumination system 300 onto the inspection target 200 and the y scanning direction of the stage 400 forms an azimuthal angle θ. In the case of FIG. 3(c), although two oblique detection systems 100 are symmetrically disposed about the y scanning direction of the stage 400, these oblique detection systems 100 are not symmetrically disposed about the incident plane.

The defect inspection apparatus according to this embodiment is configured to be able to inspect the inspection target 200 using the upward detection system 800 and the oblique detection system 100 at the same time. For example, in order to it possible to detect the same position of the inspection target by both detection systems, this defect inspection apparatus includes the oblique detection system moving unit 120 that moves the oblique detection system 100 relative to the inspection target. Alternatively, such a driving mechanism as the oblique detection system moving unit 120 may be included by the upward detection system 800 side, or such a driving mechanism may be included by each of the upward detection system 800 and oblique detection system 100.

Figure 4:
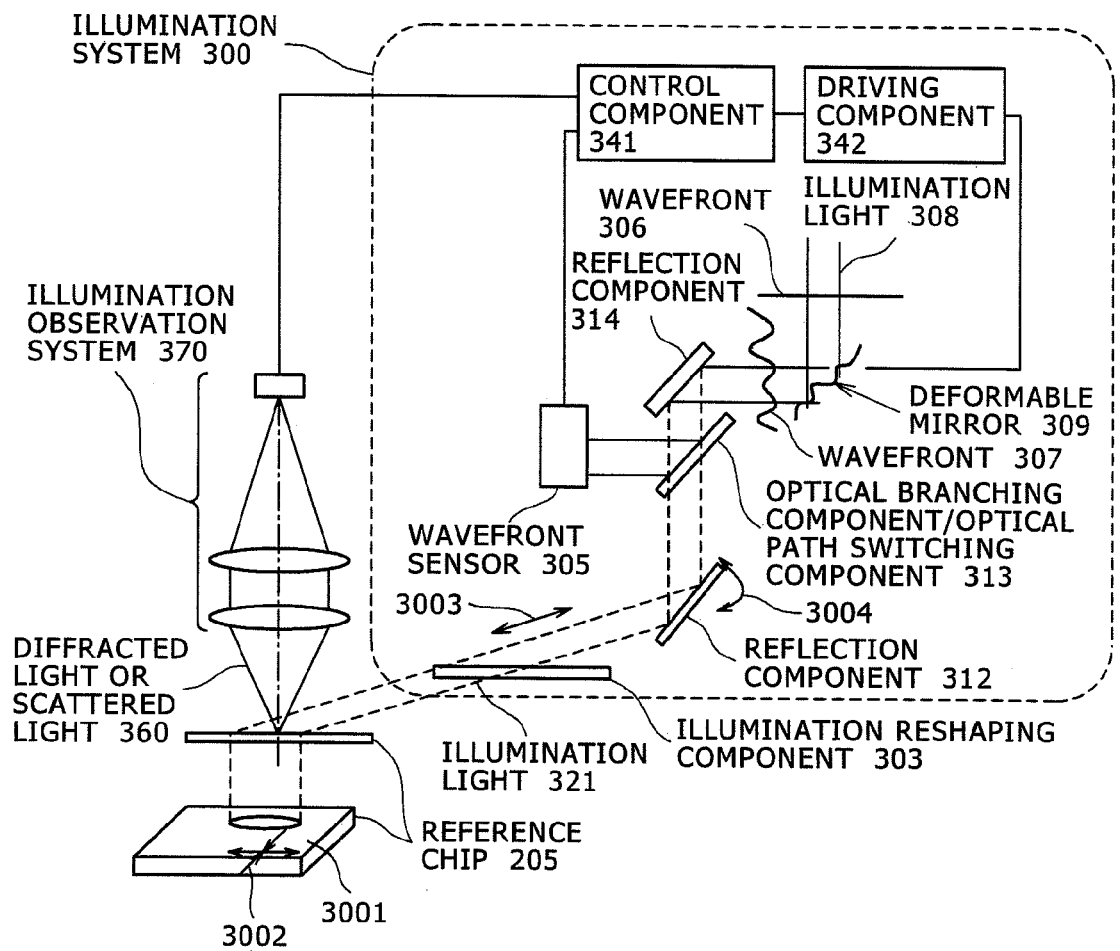
FIG. 4 is a diagram for explaining an illumination system 300 in detail.

Next, the illumination system 300 will be described in detail with reference to FIG. 4. FIG. 4 is a diagram for explaining the illumination system 300 and the illumination observation system 370 according to this embodiment. The illumination system 300 includes: a deformable mirror 309 that reshapes the wavefront 306 of illumination light 308 radiated from a light source into an arbitrary wavefront 307, and reflects the illumination light 308; a mirror 312 that is a reflection component; an optical path branching component/optical path switching component 313; a mirror 314 that is a reflection component; a wavefront sensor 305 that measures the wavefront 307 of the incident light 308 that is reflected or branched by the optical path branching component/optical path switching component 313; a control means 341 that creates data for driving the deformable mirror 309 using the wavefront measured by the wavefront sensor 305; a driving means 342 that drives the deformable mirror 309 using the data from the control means 341; and an illumination reshaping component 303 that reshapes the illumination light into linear illumination light. In this embodiment, illumination light 321 that has passed through such an illumination system 300 is irradiated onto an inspection target 200. In addition, the control component 341 and the driving component 342 can be provided separately from each other, or a combination of both components can be provided as one component. Here, a wavefront can be represented, for example, as a plane that intersects with the optical axis of light, and more concretely, can be represented as a plane perpendicular to the optical axis of the light.

The illumination system 300 will be described more concretely. After entering the deformable mirror 308, the illumination light 308, which is emitted from the light source and whose wavefront 306 is flat, is reflected. The wavefront of the illumination light 308 reflected by the deformable mirror 308 is changed from the substantially flat wavefront 306 into a wavefront 307 having undulation. The illumination light 308 reflected by the deformable mirror 308 is reflected by the reflection component 314, and enters the optical path branching component/optical path switching component 313. In this case, the undulation of the wavefront 307 represents a phase that is the inverse of the phase of the aberration of the illumination reshaping component 303. The wavefront of the light branched by the optical path branching component/optical path switching component 313 is observed by wavefront sensor 305. The wavefront observed by the wavefront sensor 305 is input into the control component 341. The light passing through the optical path branching component/optical path switching component 313 is reflected by the reflection component 312, and enters the illumination reshaping component 303. The illumination reshaping component 303 converges the light in the direction shown by an arrow 3002 (in the direction perpendicular to the plane of the page). The illumination reshaping component 303 does not converge the light in the direction shown by an arrow 3001 that is orthogonal to the arrow 3002, and irradiates the light as it is, that is, as parallel light. As a result, the light is converged in the direction shown by the arrow 3002 on the reference chip 205 (so as to have a short axis), and a substantially linear illuminated region that has a long axis in the direction shown by the arrow 3001 is formed. In addition, in this embodiment, an elevation angle at which the light is irradiated onto the reference chip 205 (or onto the inspection target 200, of course) can be changed by rotating the reflection component 312 in the direction shown by an arrow 3004 using some driving means such as a motor and by moving the illumination reshaping component in the direction shown by an arrow 3003 (in the direction parallel with the optical axis of the illumination light). Here, there are other methods that change the illumination elevation angle, and these methods will be explained in embodiments 3 to 6.

As an example of the illumination reshaping component 303, cylindrical lens, a cylindrical mirror, a diffraction optical element, a combination of one or some of the above elements and an optical lens, and the like are conceivable. In addition, as an example of arrangement of a cylindrical lens or a cylindrical mirror, there is an arrangement in which the cylindrical lens or cylindrical mirror is arranged so that the principal plane of the cylindrical lens or cylindrical mirror is parallel with the surface of the inspection target 200. As an illumination method using the illumination reshaping component 303, there is a method in which linear illumination is formed in such a way that the linear illumination intersects with an incident plane determined by the normal line of the inspection target 200 and the optical axis of the incident light, or a method in which the linear illumination is formed in the incident plane. As long as linear illumination can be formed on the inspection target 200, various methods using the illumination reshaping component 303 can be adopted.

The illumination reshaping component 303 converges the incident light, and creates the illumination light 321. In the case where the illumination light 321 is adjusted, the illumination light 321 is irradiated onto the reference chip 205. A linear illuminated region is formed on the reference chip by the illumination light 321. Scattered light from the reference chip is focused into an image and detected by the illumination observation system 370 that includes an objective lens, an imaging lens, and a one-dimensional sensor. In this case, diffracted light can be used instead of the scattered light, and a two-dimensional sensor or the so-called beam profiler can be used instead of the one-dimensional sensor. The detected image is input into the control component 341. The control component 341 creates data for driving the deformable mirror 309 using the wavefront observed by the wavefront sensor 305 and the image observed by the illumination observation system 370. (The data can be read out from a database in which candidate data are stored.) The data created by the control component 341 is changed into a signal used by the driving component 342 for driving the deformable mirror 309. The deformable mirror 309 is driven in accordance with the data from the control component 341. As a result, the wavefront 307 is changed into an arbitrary wavefront, and the shape of the linear illumination formed by the illumination light 321 is also changed.

Figure 5:
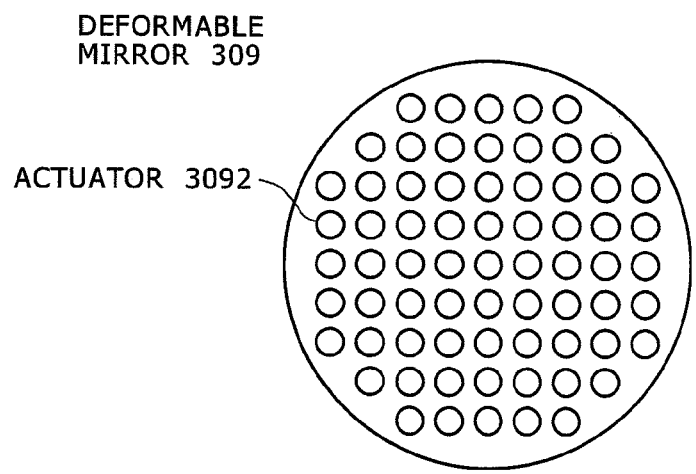
FIG. 5 is a front view of a deformable mirror 309.

Next, the deformable mirror 309 according to this embodiment will be described in detail with reference to FIG. 5, FIG. 6, and FIG. 7. FIG. 5 is a front view of the deformable mirror 309 according to this embodiment. As shown in FIG. 5, the deformable mirror 309 according to this embodiment includes a reflection board 3091 having two-dimensional spread and plural actuators 3092 disposed on the rear surface of the reflection board 3091. FIG. 6 is a cross-section view of the deformable mirror 309 according to this embodiment. The actuators 3091 can press the rear surface of the reflection board 3091. These behaviors of the actuators 3092 makes it possible to change the state of the reflection surface of the reflection board 3091 (for example, the state of the undulation of the reflection surface) arbitrarily, so that the wavefront of light, which enters the reflection board 3091 and is reflected by the reflection board 3091, can be changed arbitrarily. As a concrete example of the actuator 3092, an elastic piezoelectric element, a linear actuator, or the like can be used. Here, if the actuators 3092 are piezoelectric elements, the actuators 3092 have to include a power supply for driving the piezoelectric elements.

The deformable mirror 309 having a structure different from the above-described structure can be also conceivable. FIG. 7 is a diagram for explaining a deformable mirror including electrostatic actuators. FIG. 7(a) shows plural electrostatic actuators 3093 disposed on the rear surface of the reflection board 3091. These actuators can be fabricated using a MEMS process or the like. In addition, the actuators can be arranged in a lattice-shaped pattern, in a radial pattern, or in any other pattern. Because the strokes of the electrostatic actuators 3093 are small and the spatial resolutions of the electrostatic actuators 3093 are high, the electrostatic actuators 3093 are useful for high-accurate driving of the deformable mirror 309. In addition, as shown in FIG. 7(b), a hybrid scheme that is a combination of a scheme shown in FIG. 6 and the scheme shown in FIG. 7 can be used. In the hybrid scheme shown in FIG. 7(b), the plural electrostatic actuators 3093 are disposed on the rear surface of the reflection board 3091. In addition, the hybrid scheme includes the actuators 3092 that push the rear surface of a board 3094 disposed so as to face the rear surface of the reflection board 3091. In the hybrid scheme, the linear actuators 3092, each of which has a long stroke and a low spatial resolution, roughly drive the reflection board 3091 (perform rough driving), and the electrostatic actuators 3093, each of which has a short stroke and a high spatial resolution, perform driving more finely than the linear actuators 3092 does. In this way, the hybrid scheme has a wider driving range than the other two schemes.

Here, the wavefront sensor 305 can be a Shack-Hartmann sensor, a curvature sensor, or the like as long as it can measure the shape of a wavefront coming into the wavefront sensor 305.

Next, the procedure of illumination shaping according to this embodiment will be described with reference to FIG. 8 to FIG. 11. First, in FIG. 8(a), the control component 341 obtains the information of a wavefront (this wavefront can be referred to, for example, as a first wavefront) from the wavefront sensor 305 (at step 1101 in FIG. 11). The deformable mirror 309 is driven so that the wavefront 8001 of light entering the illumination reshaping means 303 becomes approximately in no aberration state using the information from the wavefront sensor 305 (at step 1102 in FIG. 11).

Afterward, the incident light 308 with the wavefront 8001 is irradiated onto the reference chip 205 after being reshaped in a linear shape by the illumination reshaping means 303. The illuminated shape 901 at this moment is observed by the illumination observation system 307 (at step 1103 in FIG. 11). As described above, by observing the illuminated shape 901 under the condition that the wavefront 8001 of the light is approximately in no aberration state, the state of undesired factors for light convergence such as an aberration 8010 that can not be removed for some design reason as shown in FIG. 8(b) and a wavefront aberration 8020 owing to the processing accuracy of the illumination reshaping means 303 as shown in FIG. 8(c) can be obtained. In addition, if the illumination reshaping means 303 is a cylindrical lens 8030 as shown in FIG. 8(d), there is fear that especially the shapes of both ends of the longitudinal direction of an illuminated region 8040 get turbulent.

Figure 9:
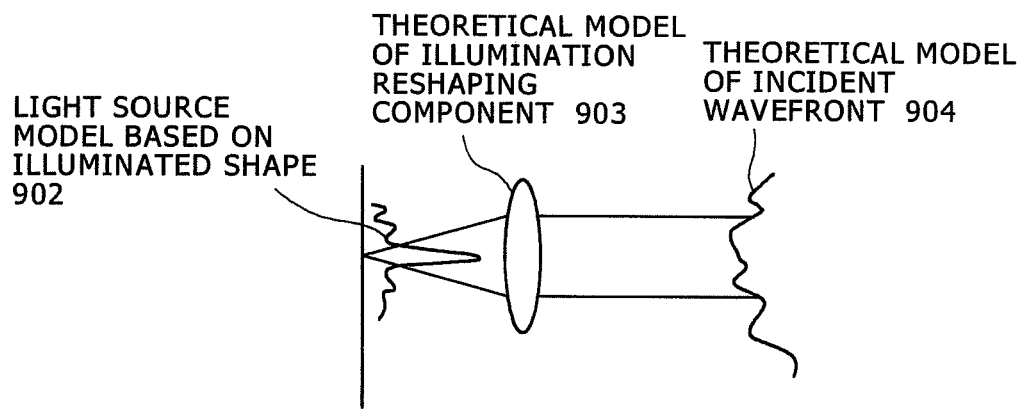
FIG. 9 is a diagram for explaining the procedure of illumination reshaping (No. 2)

FIG. 9 shows an optical simulator model in which the reference chip 205 is disposed on the object plane, the illumination reshaping means 303 and the illuminated shape 902 are modeled, and the image plane is set to an incident wavefront 904. The control component 341 disposes a light source model 902 based on the illuminated shape 901 as a light source on the reference chip 205 in accordance with the model in FIG. 9, lets the light from the light source model 902 to enter the theoretical model 903 of the illumination reshaping component 303, and calculates a wavefront 904 that has passed through the theoretical model 903 (at step 1104 in FIG. 11).

Subsequently, as shown in FIG. 10(a), the control component 341 creates data for changing the wavefront 8001, which is observed by the wavefront sensor 305 and in no aberration state, into a wavefront having an inverse phase relative to the wavefront 904 that has passed through the theoretical model 903, wherein the wavefront 904 is a wavefront onto which the factors, which are undesired for light convergence, are superimposed (at step 1105 in FIG. 11). The deformable mirror 309 is driven on the basis of these data (at step 1106 in FIG. 11), and the deformable mirror 309 changes the wavefront 8001, which is approximately in no aberration state, into a wavefront 1001 having an inverse phase relative to the wavefront 904 that has passed through the theoretical model 903 as a wavefront of light entering the illumination reshaping means 303, wherein the wavefront 1001 can be referred to, for example, as a second wavefront. The light having the wavefront 1001 is irradiated onto the reference chip 205 as linear illumination via the illumination reshaping means 303. An illuminated shape 1002 on the reference chip 205 is observed by the illumination observation system 370 (at step 1107 in FIG. 11). The control component 341 compares the observation result of the illuminated shape 901 shown in FIG. 8 with the observation result of the illuminated shape 1002, and if a desired state (for example, a state in which the linear illumination is reshaped so that its width is equal to or narrower than the width of the focused focal region as shown in FIG. 1) is verified (at step 1108 in FIG. 11), the reshaping of the illuminated region is finished (at step 1109 in FIG. 11). For example, as shown in FIG. 10(b), if the illumination reshaping means 303 that converges the light reflected by the deformable mirror 309 is the cylindrical lens 8030, because the cylindrical lens 8030 converges the illumination light 321, the shapes of both ends of the longitudinal direction of the illuminated region 8040, which is formed on the inspection target 200, does not get turbulent, so that the desired linear illumination has to be formed. If the desired state can not be obtained, it is necessary to repeat step 1106 in FIG. 11 until the desired shape is obtained. Alternatively, it is all right if the flow goes back to step 1105 in FIG. 11 to create the data again. An actual inspection shown in FIG. 11 is performed after this illumination shaping is finished (at step 1110 in FIG. 11). In other words, because the state of undesired factors for light convergence can be obtained at step 1103, by irradiating light whose wavefront is optically inverse to the wavefront onto which the undesired factors for light convergence is superimposed (for example, the wavefront onto which the undesired factors for light convergence are superimposed can be referred to as a wavefront having the inverse phase), it can be expected that the desired linear illumination is formed.

Thanks to the above procedure, the influence, which is caused by an aberration that can not be removed for some design reason, a wavefront aberration owing to the processing accuracies of optical elements themselves that are used for convergence, and the like, can be reduced, so that it becomes possible to make the state of an illuminated shape 905 come near to a preferred state for the inspection (for example, a state in which the linear illumination is reshaped so that its width is equal to or narrower than the width of the focused focal region as shown in FIG. 1). According to this embodiment, the wavefront aberration of illumination light can be reduced, and the line width of an illuminated region can be miniaturized, with the result that the sensitivity of the defect inspection performed by the oblique detection system can be improved.

Although the example in which the illumination reshaping is automatically adjusted by the control unit 341 has been described above, the illumination reshaping may also be configured to be performed by an operator who manually performs the operations of the control unit 341 using various display devices and input devices. Alternatively, the illumination reshaping may also be configured in such a way that a part of the above illumination reshaping procedure is performed by the control unit 341, and the other part is performed by an operator. In addition, it is also all right that at least one of the upward detection system 800 and the oblique detection system 100 includes the function of the observation optical system 370.

Second Embodiment

Next, a second embodiment will be described. In the description about the second embodiment, parts of the second embodiment different from those of the first embodiment will mainly be described. The first embodiment includes the deformable 309 mirror that is an example of system for changing a wavefront, and the illumination reshaping component 303 that forms linear illumination. In other words, it can be said that optical systems or optical elements independent from each other are respectively in charge of the function for changing a wavefront and the function for forming linear illumination. This embodiment is characterized in that one optical system is in charge of both function for changing a wavefront and function for forming linear illumination.

This embodiment will be described more concretely. FIG. 12 is a diagram for explaining this embodiment. This embodiment allows a deformable mirror 309 itself to include the function for reshaping illumination (that is, the function for forming linear illumination) without using the illumination reshaping component 303 of the first embodiment. In other words, for example, as shown in FIG. 12, plural actuators 3092 disposed on the rear surface of a reflection component 601 are driven, so that the reflection component 601 forms the reflection plane of a cylindrical mirror. In this case, it can be said that the deformable mirror 309 according to this embodiment is a deformable cylindrical mirror including both function for changing a wavefront and function for forming linear illumination. Such a deformable mirror 309 is especially effective for forming linear illumination using light of a short wavelength. In addition, plural deformable mirrors 309 according to this embodiment may also be disposed in the optical path of an illumination system. Further, a total reflection illumination optical system can be configured using the deformable mirrors 309 and plural reflection optical elements such as mirrors. Here, a hybrid type deformable mirror as shown in FIG. 7(a) can be used as the deformable mirror 309 according to this embodiment.

Third Embodiment

Next, a third embodiment will be described below. In order to highly sensitively detect various defects existing on an inspection target, an optimal illumination condition (determined by, for example, an azimuthal angle, an elevation angle, a wavelength, and the polarization of light irradiated onto the inspection target) varies in accordance with various kinds of defects. This embodiment is achieved with this point in mind, and characterized in that it includes an illumination condition changing system in which a deformable mirror changes the wavefront of light in accordance with the variation of the illumination condition. In the description about the third embodiment, parts of the third embodiment different from those of the first embodiment will mainly be described.

Figure 13:
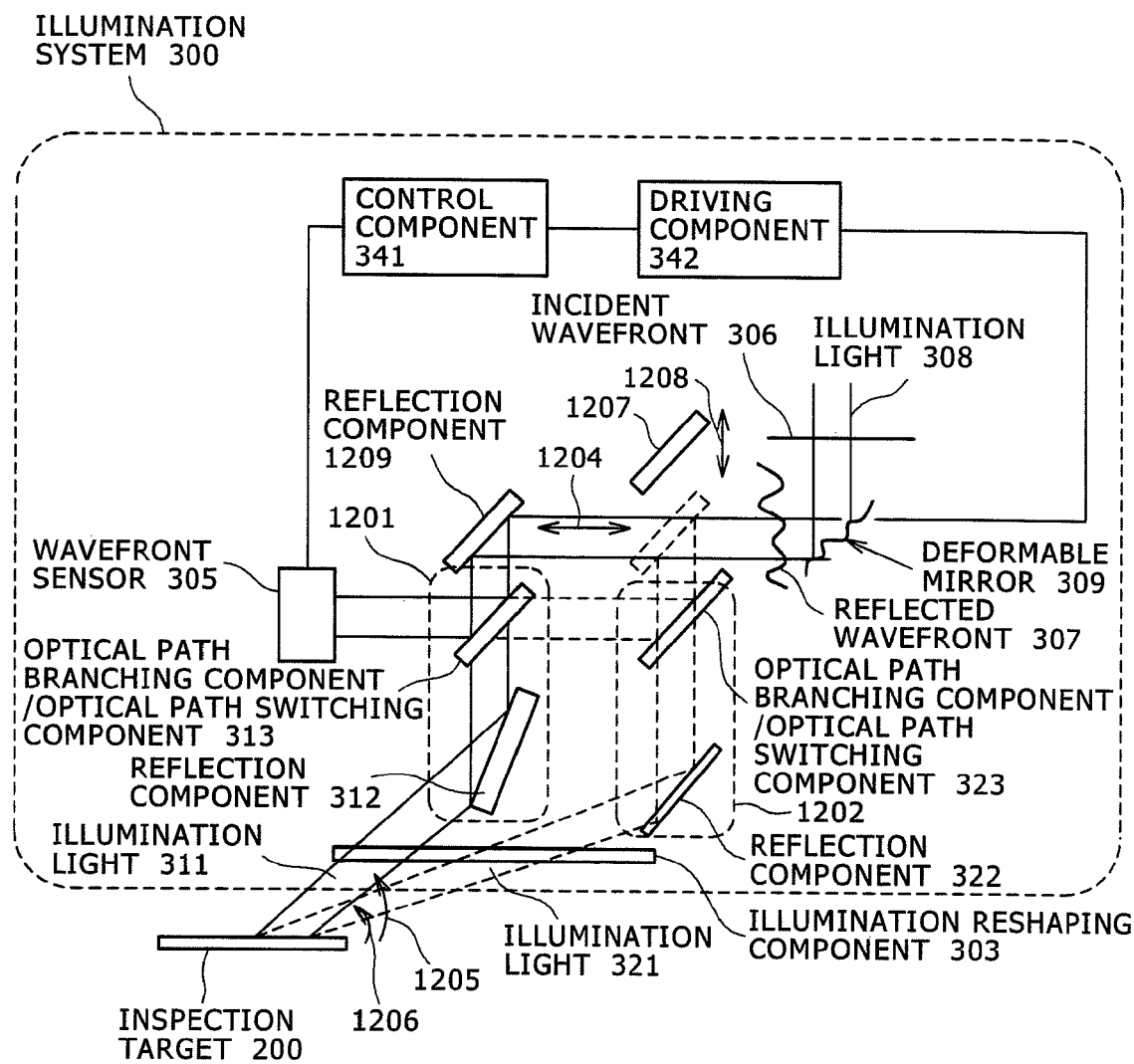
FIG. 13 is a diagram for explaining a third embodiment.

FIG. 13 is a diagram for explaining this embodiment. This embodiment includes a first elevation angle illumination system 1201 for forming linear illumination on an inspection target 200 at a first elevation angle 1205 and a second elevation angle illumination system 1202 for forming linear illumination on the inspection target 200 at a second elevation angle 1206 that is lower than the first elevation angle 1205 in the optical path between a deformable mirror 309 and a illumination reshaping component 303. In addition, this embodiment includes a reflection component 1203, such as a mirror, for guiding the light reflected, by the deformable mirror 309 to the first elevation angle illumination system 1201 or to the second elevation angle illumination system 1202 between the first elevation angle illumination system 1201 and the second elevation angle illumination system 1202. The mirror can be moved in the direction shown by an arrow 1204. The first elevation angle illumination system 1201 includes an optical path branching component/optical path switching component 313 for guiding the light reflected by the reflection component 1203 to a wavefront sensor 305, and the reflection component 312, such as a mirror, for guiding the light that passes through the optical path branching component/optical path switching component 313 to the illumination reshaping component 303. The second elevation angle illumination system 1202 includes an optical path branching component/optical path switching component 323 for guiding the light reflected by the reflection component 1203 to the wavefront sensor 305, and a reflection component 322, such as a mirror, for guiding the light that passes through the optical path branching component/optical path switching component 323 to the illumination reshaping component 303.

In this embodiment, in the case where the reflection component 1203 guides the light to the first elevation angle illumination system 1201, the deformable mirror 309 adjusts a reflection wavefront 307 so that the width of linear illumination formed by illumination light 311 is reshaped at the first elevation angle 1205 so as to be equal to or narrower than the width of the focused focal region. In addition, in the case where the reflection component 1203 guides the light to the second elevation angle illumination system 1202, the deformable mirror 309 adjusts the reflection wavefront 307 so that the width of linear illumination formed by illumination light 321 is reshaped at the second elevation angle 1206 so as to be equal to or narrower than the width of the focused focal region.

The adjustment of the wavefront can be performed in the following way. In advance of the inspection, the adjustment method disclosed in the first embodiment is performed in both cases where linear illumination is formed on the inspection target 200 at the first elevation angle 1205 and where linear illumination is formed on the inspection target 200 at the second elevation angle, and first data for forming the linear illumination on the inspection target 200 at the first elevation angle 1205 and second data for forming the linear illumination on the inspection target 200 at the second elevation angle 1206 are respectively stored in the control component 341. In the inspection, after the first data or the second data is read out in accordance with the movement of the reflection component 1203, the deformable mirror 309 may be driven using the read-out data. Other parts of this embodiment are the same as those of the first embodiment. According to this embodiment, the illumination elevation angle can be changed, so that it becomes possible to perform a more highly sensitive inspection. In addition, in this embodiment, a newly installed reflection component 1207 may be taken into or taken out of the optical path of the second elevation angle illumination system 1202 in the direction shown by an arrow 1208 while the reflection component 1203 is fixed in the optical path of the first elevation angle illumination system 1201 instead of being moved.

Fourth Embodiment

Figure 14:
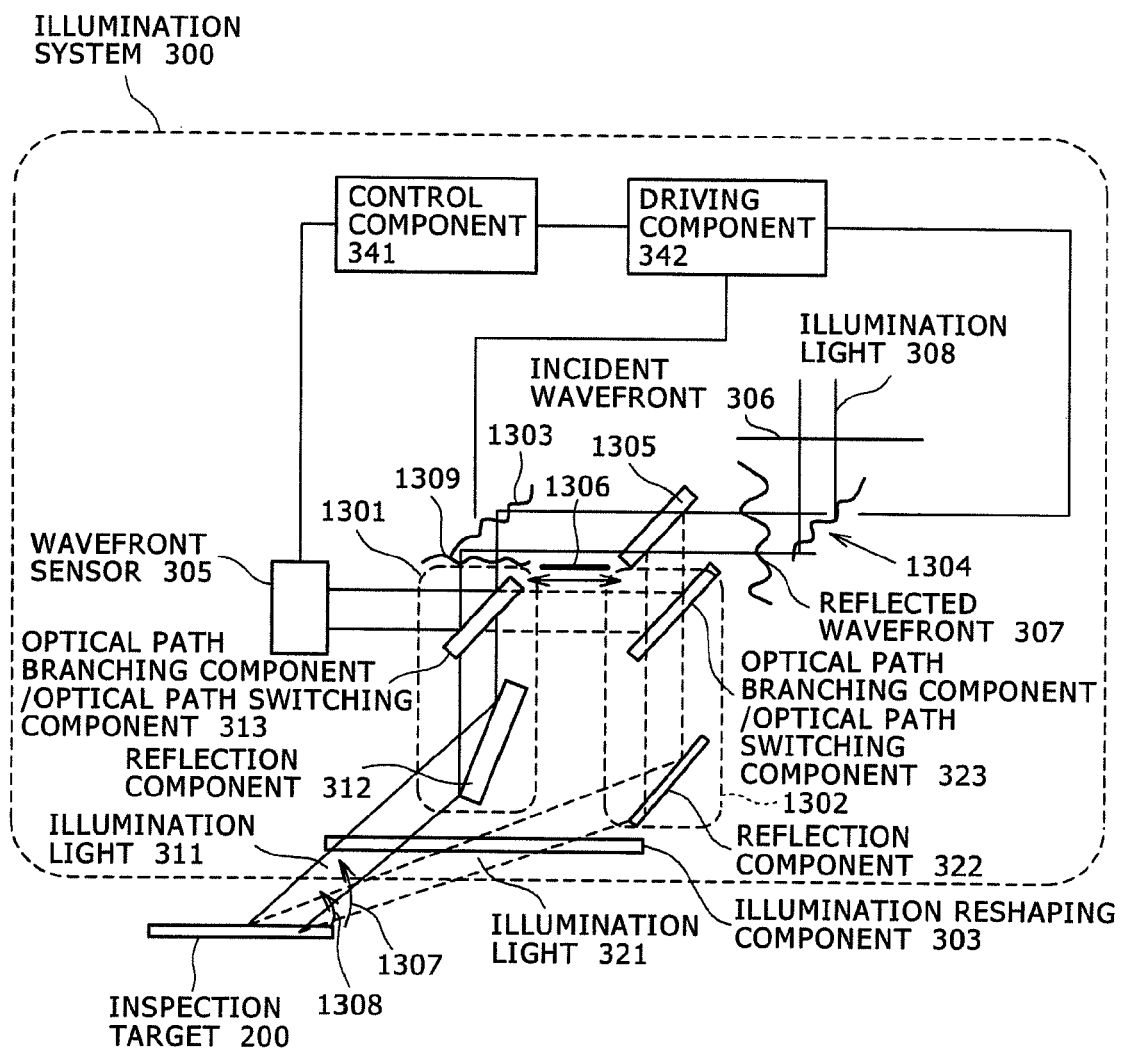
FIG. 14 is a diagram for explaining a fourth embodiment.

Next, a fourth embodiment will be described with reference to FIG. 14. In the third embodiment, an example in which the illumination elevation angle is changed has been described. This embodiment shows an example in which plural pieces of light are irradiated at plural elevation angles substantially at the same time. In the description about this embodiment, parts of the fourth embodiment different from those of the first and second embodiments will mainly be described.

This embodiment is characterized in that it includes an optical path branching component 1305 and a first deformable mirror 1303 that reflects light that passes through the optical path branching component 1305 instead of the reflection component 1203 described in the third embodiment.

This embodiment will be described more concretely below. In this embodiment, illumination light 308 with an incident wavefront 306 is reflected by a second deformable mirror 1304. The light whose wavefront is changed into a reflection wavefront 307 by the deformable mirror 1304 enters the optical path branching component 1305. The light that passes through the optical path branching component 1305 enters the first deformable mirror 1303. The light whose wavefront is further changed by the first deformable mirror 1303 enters a first elevation angle illumination system 1301 for forming linear illumination on the inspection target 200 at a first elevation angle 1307. The light reflected by the optical path branching component 1305 enters a second elevation angle illumination system 1302 for forming linear illumination on the inspection target 200 at a second elevation angle 1308 that is lower than the first elevation angle 1307. The configurations of the first elevation angle illumination system 1301 and the second elevation angle illumination system 1302 are respectively the same as those of the first elevation angle illumination system and the second elevation angle illumination system shown in the third embodiment.

In this embodiment, the first deformable mirror 1303 adjusts a reflection wavefront 1309 so that the width of linear illumination formed by illumination light 311 is reshaped at the first elevation angle 1307 so as to be equal to or narrower than the width of the focused focal region. The second deformable mirror 1304 adjusts the reflection wavefront 307 so that the width of linear illumination formed by illumination light 321 is reshaped at the second elevation angle 1308 so as to be equal to or narrower than the width of the focused focal region.

In this embodiment, the adjustment of linear illumination can be performed in the following way. (1) First, the optical path of the first elevation angle illumination system 1301 is shielded by a shutter 1306, and the wavefront of light that passes through the optical path branching component/optical path switching component 323 in the second elevation angle detection system 1302 is observed by the wavefront sensor 305. (2) Subsequently, using the adjustment method disclosed in the first embodiment, the reflection wavefront 307 is adjusted so that the width of linear illumination irradiated at the second elevation angle 1308 is reshaped so as to be equal to or narrower than the width of the focused focal region. (3) Next, the optical path of the second elevation angle illumination system 1302 is shielded by the shutter 1306, and the wavefront of light that passes through the optical path branching-component/optical path switching component 313 in the first elevation angle detection system 1301 is observed by the wavefront sensor 305. (4) Subsequently, using the adjustment method disclosed in the first embodiment, the reflection wavefront 1309 is adjusted so that the width of linear illumination irradiated at the first elevation angle 1307 is reshaped so as to be equal to or narrower than the width of the focused focal region.

In the actual inspection, first data for forming the linear illumination on the inspection target 200 at the first elevation angle 1307 and second data for forming the linear illumination on the inspection target 200 at the second elevation angle 1308 are respectively stored in a control component 341, and after the first data and the second data are read out, the first deformable mirror 1303 and the second deformable mirror 1304 can be driven respectively using the read-out first data and second data.

According to this embodiment, pieces of light are irradiated at plural elevation angles onto the inspection target 200 at the same time, so that it becomes possible to perform a more highly sensitive inspection.

Fifth Embodiment

Figure 15:
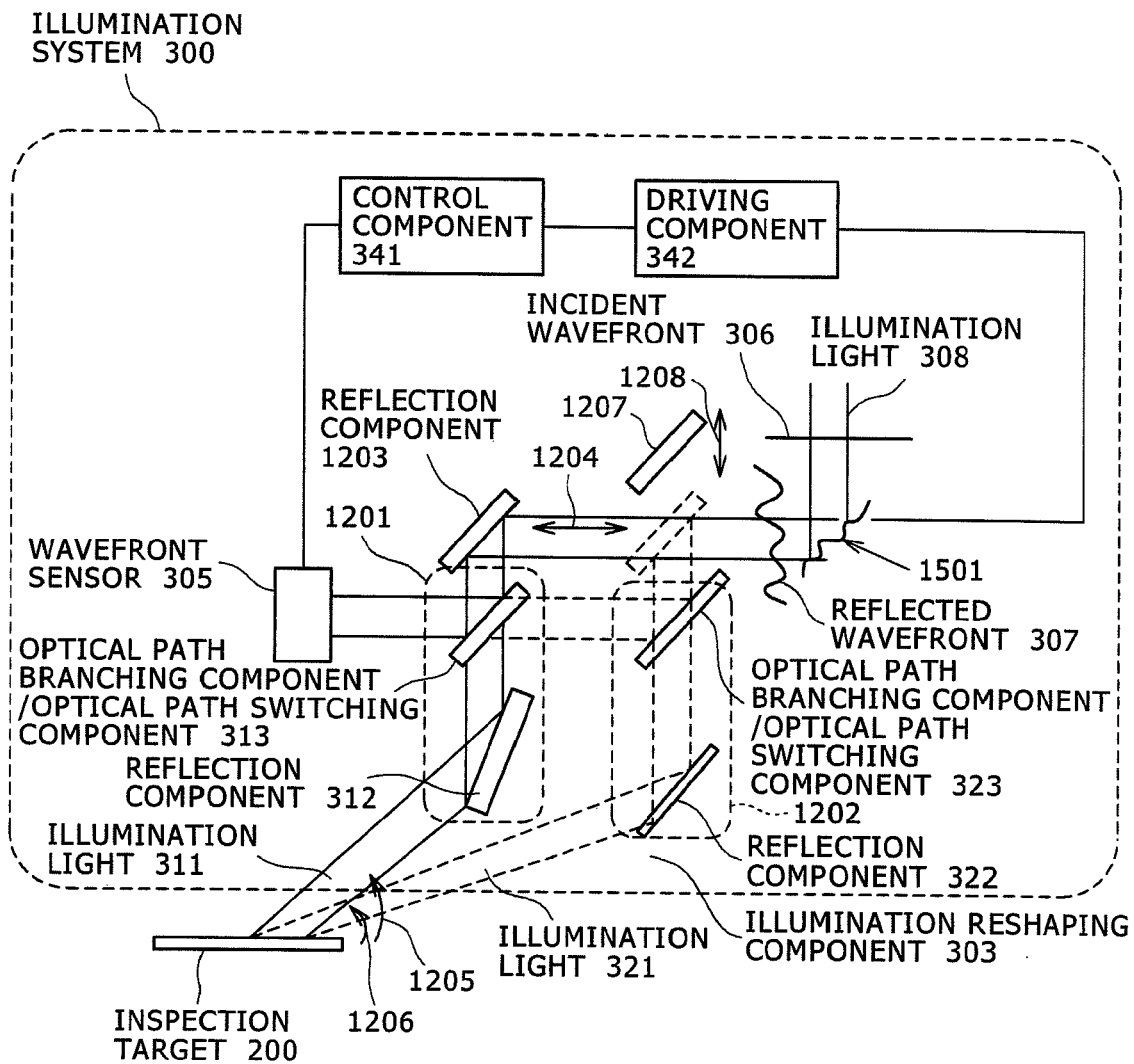
FIG. 15 is a diagram for explaining a fifth embodiment.

A fifth embodiment will be described below. FIG. 15 is a diagram for explaining the fifth embodiment. The fifth embodiment is characterized in that the deformable cylindrical mirror explained in the second embodiment is used instead of the illumination reshaping component 303 and the deformable mirror 309 that are explained in the third embodiment, and pieces of light are selectively irradiated onto the inspection target at plural elevation angles. In the fifth embodiment, a more highly sensitive inspection can be performed using light of a shorter wavelength.

Sixth Embodiment

Figure 16:
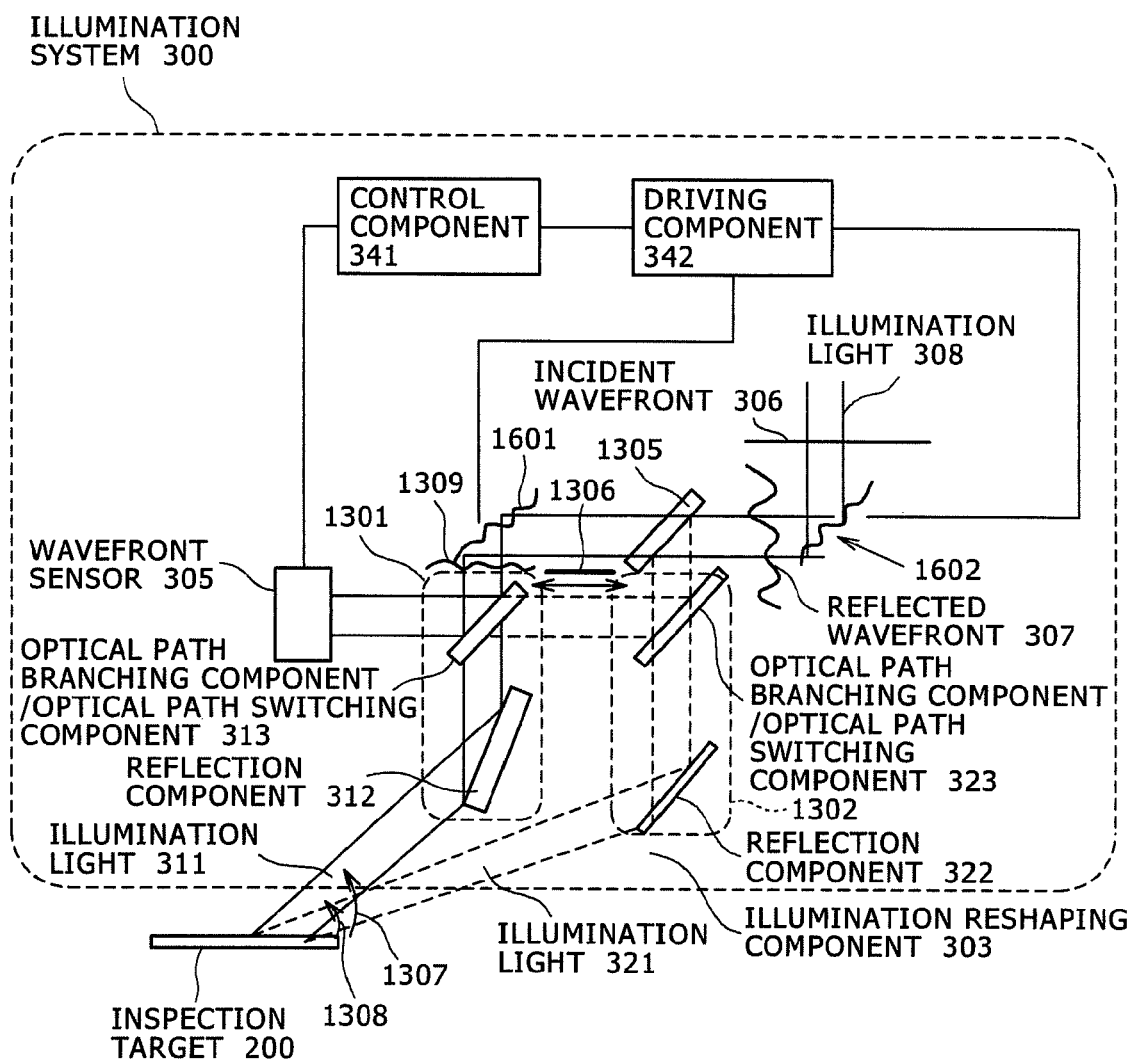
FIG. 16 is a diagram for explaining a sixth-embodiment.

Next, a sixth embodiment will be described below. FIG. 16 is a diagram for explaining the sixth embodiment. The sixth embodiment is characterized in that a first deformable cylindrical mirror 1601 and a second the deformable cylindrical mirror 1602, such as explained in the second embodiment, are used instead of the illumination reshaping component 303, the first deformable mirror 1303, and the second deformable mirror 1304 that are explained in the fourth embodiment, and pieces of light are irradiated approximately at the same time onto the inspection target at plural elevation angles. In the sixth embodiment, a more highly sensitive inspection can be performed using light of a shorter wavelength. In the fourth embodiment to the seventh embodiment, although the descriptions have been made under the assumption that one illumination reshaping component 303 is used, linear illumination may also be formed at plural elevation angles by preparing the same number of the illumination reshaping components 303 as the number of the elevation angles at which pieces of illumination light are irradiated.

Seventh Embodiment

A seventh embodiment will be described below. In the above described embodiments, it can be said that, for example, it is preferable for the optical location of the wavefront sensor 305 to be near to linear illumination. This is because to observe a wavefront at a location nearer to the linear illumination makes it possible to observe the state of the wavefront that is just before the actual formation of the linear illumination. This embodiment is achieved with this point in mind.

Figure 17:
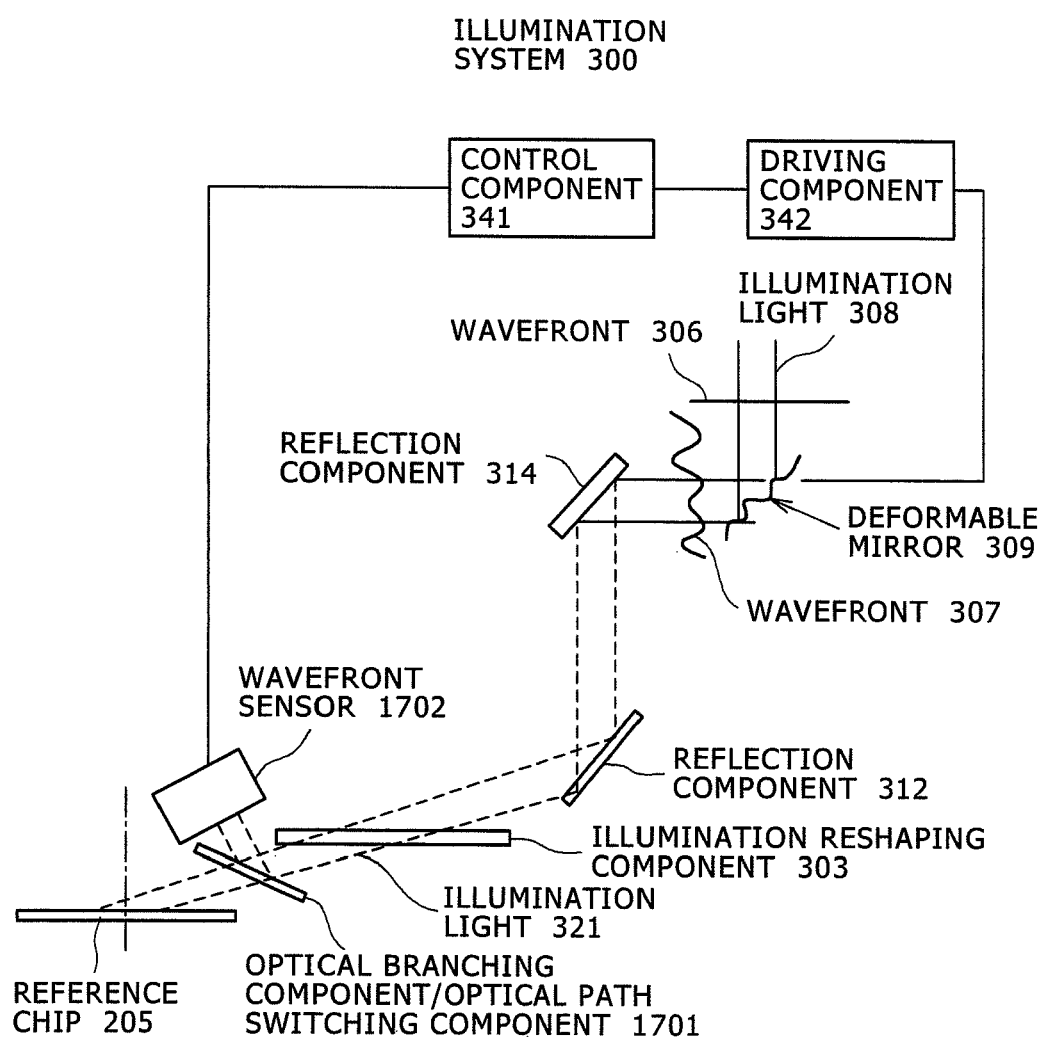
FIG. 17 is a diagram for explaining a seventh embodiment.

FIG. 17 is a diagram for explaining this embodiment. In the first embodiment to the sixth embodiment, the optical branching component/optical path switching component and the wavefront sensor are disposed in the optical path located before the illumination reshaping component 303 (in other words, in the optical path located farther than the illumination reshaping component 303 viewed from the inspection target 200). In this embodiment, an optical branching component/optical path switching component 1701 and a wavefront sensor 1702 are disposed in an optical path located after an illumination reshaping component 303 (in other words, in an optical path located nearer than the illumination reshaping component 303 viewed from an inspection target 200). In order to reshape linear illumination, the adjustment method disclosed in the first embodiment can be performed while the linear illumination is radiated onto a reference chip 205.

According to this embodiment, it becomes possible to observe the state of a wavefront that is just before the actual formation of the linear illumination and to feed back the observed wavefront to driving a deformable mirror, so that narrower linear illumination can be formed.

Eighth Embodiment

Figure 18:
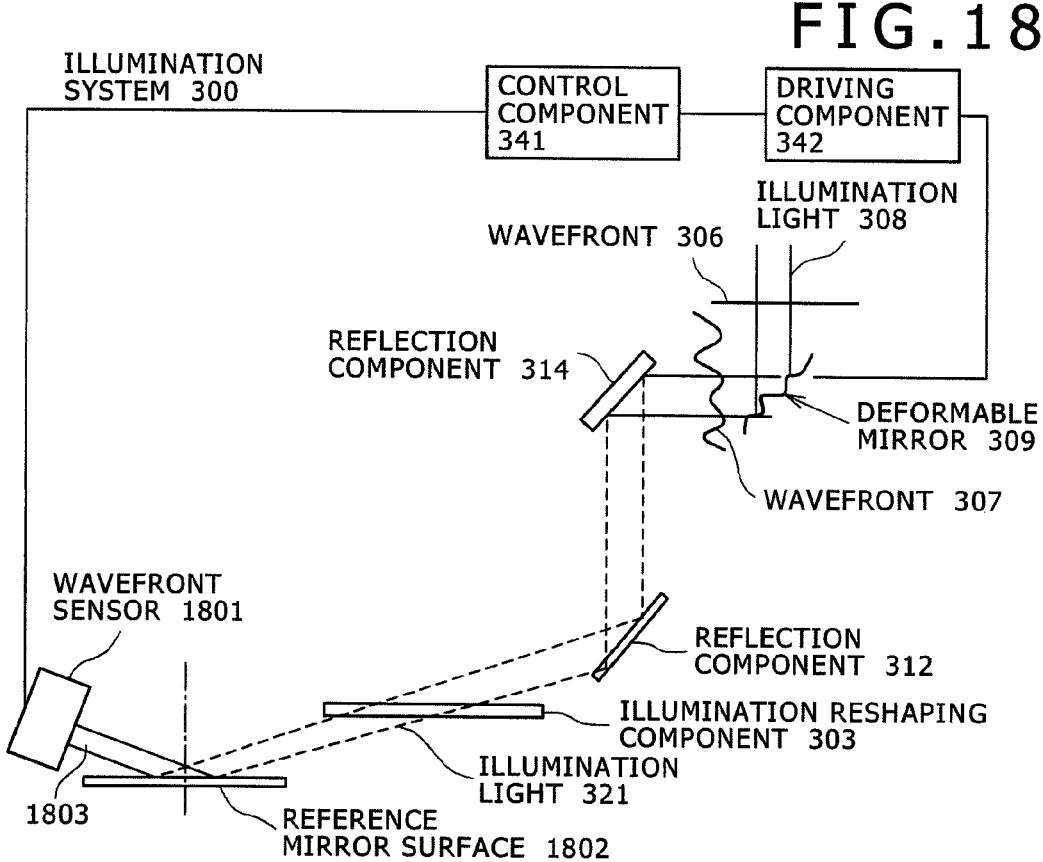
FIG. 18 is a diagram for explaining an eighth embodiment.

An eighth embodiment will be described below. Another variation of the location of the wavefront sensor can be thought of. FIG. 18 is a diagram for explaining the eighth embodiment. This embodiment includes a reference mirror surface 1802 having a polished mirror surface and a wavefront sensor 1801 disposed in the regular reflection position of the incident angle of illumination light 321 instead of the reference chip, the optical branching component/optical path switching component that have been described in the first embodiment to the seventh embodiment.

The eighth embodiment will be described more concretely. The reference mirror surface 1802 is polished so as to be able to reflect the illumination light, and it is disposed in an arbitrary position such as on the stage 400 or on the inspection target 200 shown in FIG. 3. The wavefront sensor 1801 is disposed in the regular reflection position so that the wavefront sensor 1801 can detect the regular reflection light reflected from the reference mirror surface 1802, and the wavefront sensor 1801 observes the wavefront of the regular reflection light 1803.

Ninth Embodiment

Figure 19:
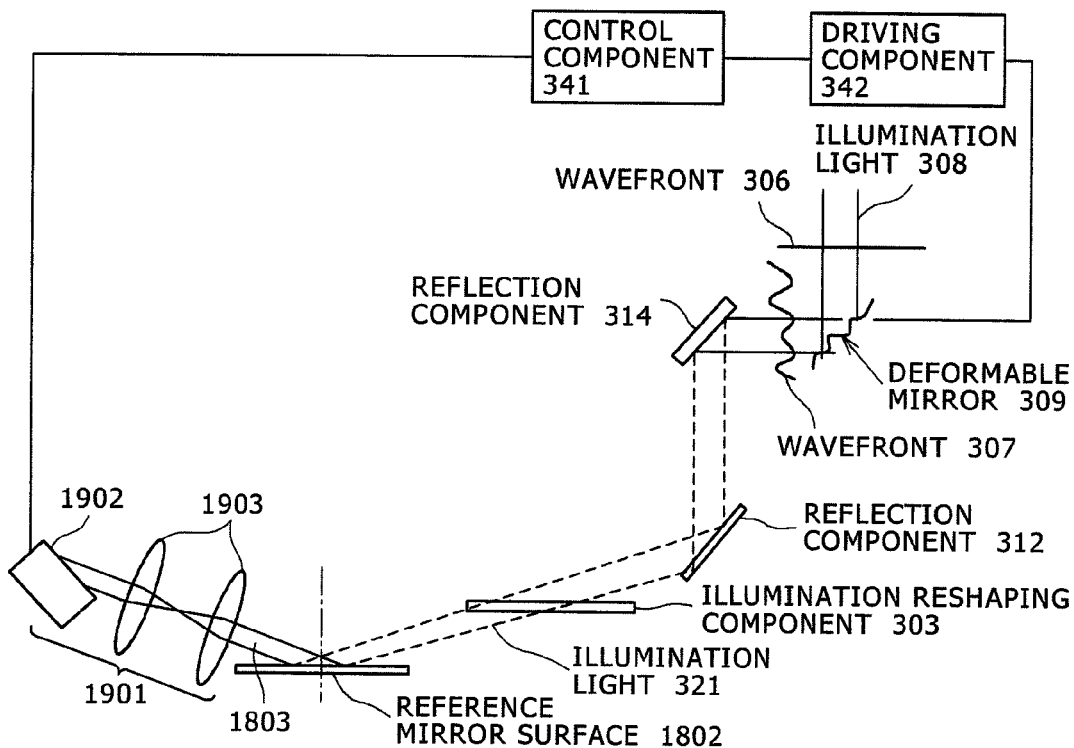
FIG. 19 is a diagram for explaining a ninth embodiment.

A ninth embodiment will be described below. The ninth embodiment is characterized in that it includes an illumination observation system 1901 that detects regular reflection light instead of the above-described illumination observation system 307 that detects scattered light and diffracted light. In the description about this embodiment, parts of this embodiment different from those of other embodiments will mainly be described. FIG. 19 is a diagram for explaining this embodiment. In this embodiment, the reference mirror surface 1802 described in the eighth embodiment is used. An inspection apparatus according to this embodiment includes an illumination observation system 1901 that detects the regular reflection light 1803 reflected by the reference mirror surface 1802 as an image. The illumination observation system 1901 includes an imaging optical system 1903 such as a lens that focuses the regular reflection light 1803 into an image, and a sensor 1902 that detects the focused reflection light image. In addition, there is a case where the sensor 1902 includes plural pixels. As such a sensor 1902, the so-called beam profiler can be adopted. The regular reflection light image observed by the illumination observation system 1901 is transmitted to a control component 341, and is used for reshaping the illuminated shape described in the first embodiment (to put it more concretely, it is used at step 1103, step 1107, step 1108, and the like in FIG. 11).

Tenth Embodiment

Figure 20:
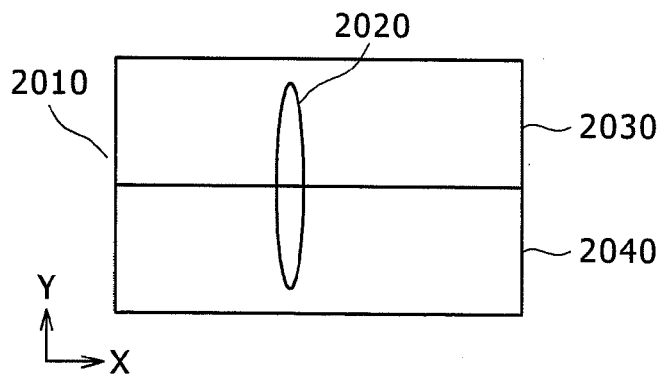
FIG. 20 is a diagram for explaining a tenth embodiment (No. 1).

A tenth embodiment will be described below. In the inspection of a wafer on which circuit patterns are formed, there is a case where the heights of the circuit patterns formed on the wafer are different from each other. FIG. 20 is a top view of a wafer on which patterns are formed. In FIG. 20, in the case where a pattern 2030 having a certain height and a pattern 2040 having its height lower than that of the pattern 2030 are formed on the wafer, if linear illumination 2020 is irradiated onto both patterns redundantly, it may undesirably happen that the linear illumination 2020 is properly focused on one pattern and it is defocused on the other pattern. This embodiment is achieved with this point in mind, and is characterized in that the wavefront of light entering an optical element that converges the light is changed in accordance with the heights of patterns.

Figure 21:
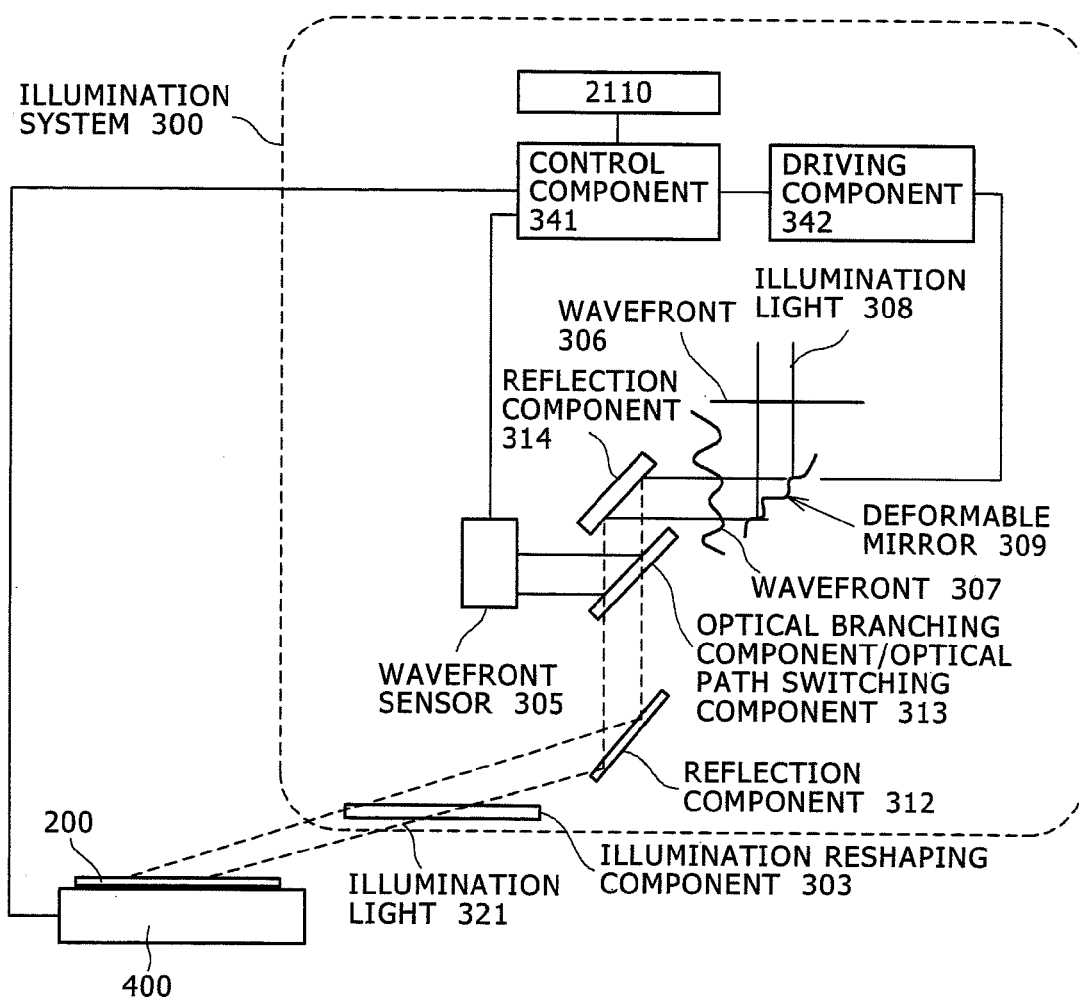
FIG. 21 is a diagram for explaining the tenth embodiment (No. 2).

This embodiment will be described more concretely. In the description about this embodiment, parts of this embodiment different from those of other embodiments will be described in particular. FIG. 21 is a diagram for explaining an inspection apparatus according to this embodiment, and particularly for explaining an illumination system 300 of the inspection apparatus. A database 2110 that stores design information about circuit patterns formed on an inspection target 200 is coupled to a control component 341 that creates data for driving a deformable mirror 309. In addition, the scanning information of a stage 400 (information showing how long the stage 400 has moved in the x and y directions) is transmitted to the control component 341. In other words, if the dimensions of the linear illumination is known, the location of the linear illumination on the inspection target 200 can be known from the scanning information of the stage 400.

The control component 341 checks the known dimensions of the linear illumination, the design information from the design information database 2110, and the scanning information from the stage 400, and judges how much part of the linear illumination is irradiated onto each circuit pattern. Subsequently, the control component 341 drives the deformable mirror 309 in accordance with the height of each pattern.

In addition, this embodiment will be described more concretely. FIG. 22 is a diagram for explaining this embodiment more in detail. Further, in FIG. 22(a), components disposed in optical paths between the deformable mirror 309 and an illumination reshaping means 303 are omitted for ease of explanation. In FIG. 22(a), it will be assumed that a pattern 2030 having a high height and a pattern 2040 having its height lower than the height of the pattern 2030 are formed in the y scanning direction on the inspection target 200. The control component 341 checks the known dimensions of the linear illumination, the design information from the design information database 2110, and the scanning information from the stage 400, and judges whether the linear illumination is redundantly irradiated onto both the high pattern 2030 and the low pattern 2040 or not (this judgment can be done either before or during the inspection). In the initial state shown in FIG. 22(a), it will be assumed that the linear illumination is focused on both focal point 2050 and focal point 2200 that are as high as the surface of the low pattern 2040. If the control component 341 judges that the linear illumination is redundantly irradiated onto both the high pattern 2030 and the low pattern 2040, the control component 341 drives the deformable mirror 309 so that one illuminated region of the linear illumination that overlaps the high pattern 2030 is focused on a focal point 2060 instead of the focal point 2050. On the other hand, the control component 341 drives the deformable mirror 309 so that the other illuminated region of the linear illumination that overlaps the low pattern 2040 is focused on the focal point 2200. With the above function of the control component 341, two regions with focus positions different from each other are formed in one linear illumination. Scanning in the direction shown by an arrow 2080 is performed with the linear illumination that is focused on the focal point 2060 in the case of the high pattern 2030 and is focused on the focal point 2200 in the case of the low pattern 2040.

In addition, in this embodiment, a step 2070 is also taken into consideration. In other words, there may be a case where, if the step 2070 is too small to substantially influence the focusing of the linear illumination, the inspection is continued without changing the above-described change of the wavefront. Further, there may be a case where a circuit pattern having two patterns whose heights are different from each other not only in the y scanning direction, but also in the x scanning direction is formed. In this case, it is all right if the wavefront is changed in accordance with the heights of the patterns in the x scanning direction. In this embodiment, although the design information has been used, it is also all right if the image of the illuminated region actually measured in advance or information obtained by a separately-installed auto-focus system or the like is used instead of using the design information. As described above, this embodiment is characterized, for example, in that it changes the wavefront of light entering an optical element used for converging the light in accordance with the heights of patterns. In other words, this embodiment is characterized in that it includes one illuminated region in which plural illuminated regions each of which has its own focal point are formed. According to this embodiment, even in the case where there are patterns whose heights are different from each other, a highly sensitive inspection can be performed.

Eleventh Embodiment

An eleventh embodiment will be described below. As factors that have undesirable influence on the formation of linear illumination, there are environmental factors in an apparatus, especially environmental factors in an illumination system (such as temperature, air pressure, humidity) other than an aberration that can not be removed for some design reason, and a wavefront aberration owing to the processing accuracies of optical elements themselves that are used for convergence. This embodiment is achieved with this point in mind, and is characterized in that it changes the wavefront of light entering optical elements used for converging the light in accordance with environmental factors in an apparatus, especially environmental factors in an illumination system (such as temperature, air pressure, humidity).

Figure 23:
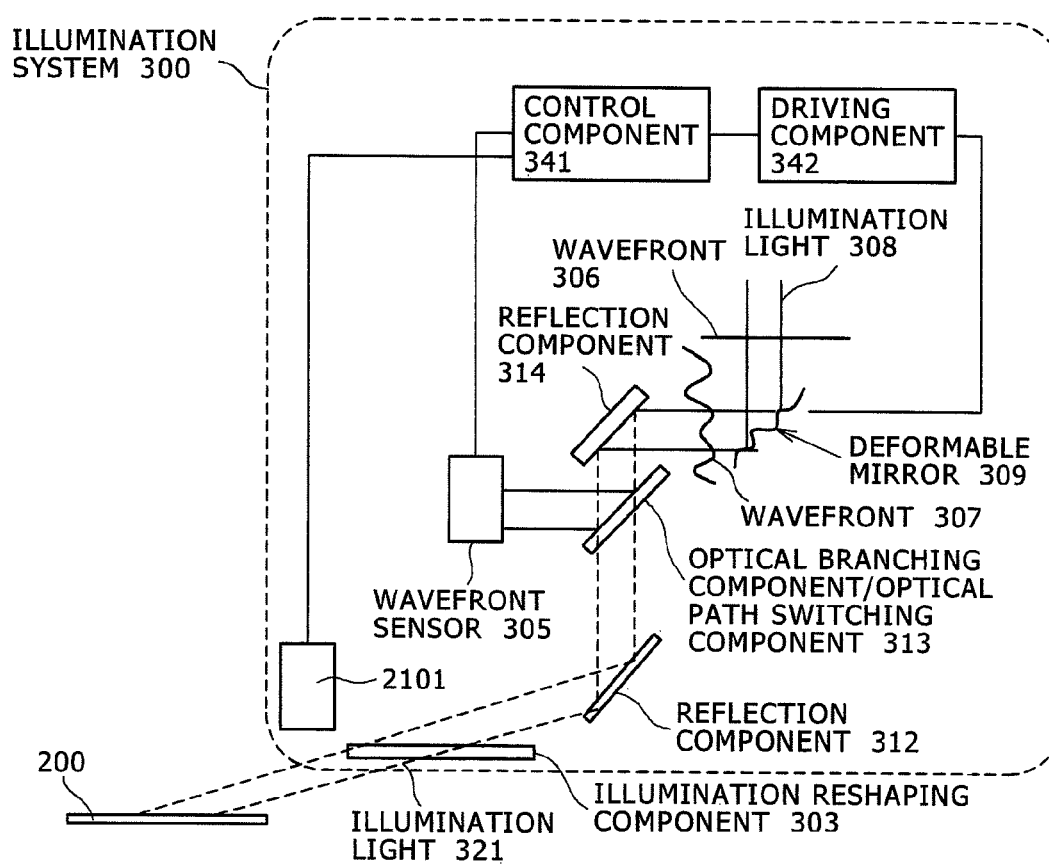
FIG. 23 is a diagram for explaining an eleventh embodiment.

This embodiment will be described more concretely below. FIG. 23 is a diagram for explaining this embodiment. This embodiment includes an environmental measurement unit 2101 for measuring environmental factors in an illumination system 300 (for example, at least one of temperature, air pressure, and humidity). Plural environmental measurement units 2101 may be installed in the illumination system 300. The measurement result of the environmental measurement unit 2101 are transmitted to a control component 341, and the control component 341 drives a deformable mirror 309 in accordance with this measurement result. In other words, the wavefront 307 of light reflected by the deformable mirror 309 is changed in accordance with the result of the environmental measurement unit 2102.

Figure 24:
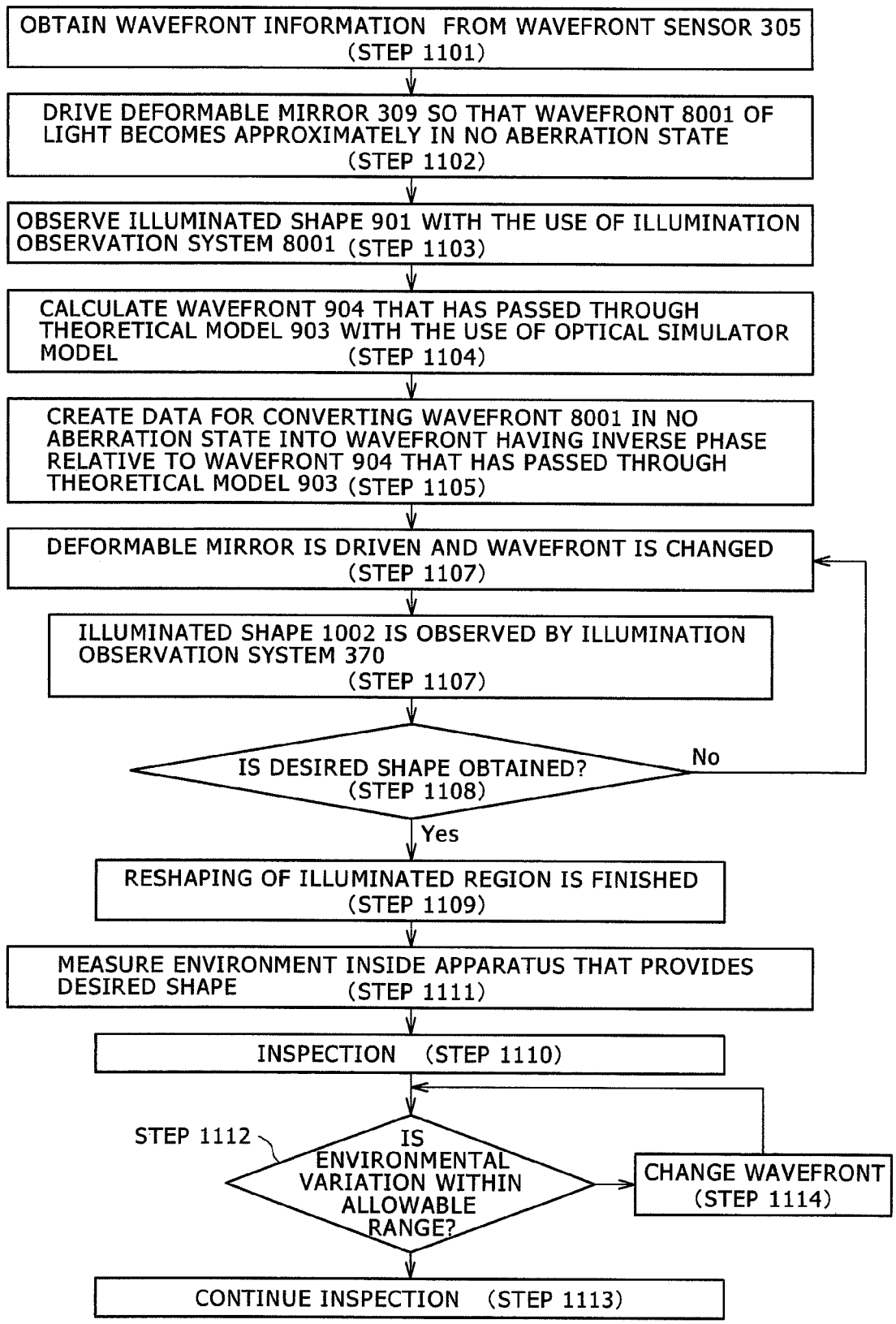
FIG. 24 is a flowchart for explaining the eleventh embodiment.

In addition, this embodiment will be concretely explained with reference to the flowchart in FIG. 24. Step 1101 to step 1110 of the flowchart in FIG. 22 are the same as those of the flowchart in FIG. 11 according to the first embodiment. In this embodiment, environmental factors in the apparatus when the desired shape of linear illumination is obtained is measured by the environmental measurement unit 2101, and the measurement result is stored in the memory in the control component 341. After an inspection starts at step 1110, the environmental measurement unit 2101 periodically transmits a measurement result to the control component 341. The control component 341 judges whether the measurement result is within the allowable range or not (at step 1112), and if the measurement result is within the allowable range, the inspection is continued (at step 1113). If the measurement result is not within the allowable range, the control component 341 drives the deformable mirror 309, and changes the wavefront 307 of the light reflected by the deformable 309. To explain it more concretely, the control component 341 obtains the relationship between variations of the environmental factors in the apparatus and variations of the wavefront 307 when the desired shape of the linear illumination is obtained, and the control component 341 drives the deformable mirror 309 on the basis of this relationship. According to this embodiment, even in the case where there are variations of the environmental factors in the apparatus, a highly sensitive inspection can be performed.

Although several embodiments have been described above, the present invention is not limited to these embodiments. In the above-described embodiments, it has been described that the wavefront of light that enters an optical element used for forming linear illumination is adjusted so that the linear illumination is reshaped so as to have a width equal to or narrower than the focused focal region. However, the present invention can be applied to the case where an illumination region other than the linear illumination is formed. In the other words, to obtain the wavefront of incident light used for obtaining a desired illuminated shape or to change the wavefront of the incident light used for obtaining a desired illuminated shape are within the limits of the idea of the present invention.

In addition, the above-described wavefront sensors and deformable mirrors can be adopted in a detection optic system such as an oblique detection system, and an upward detection system. Further, the present invention can be applied to a surface inspection apparatus that inspects a mirror surface wafer. The present invention can be applied not only to a wafer, but also town inspection apparatus for inspecting various boards, and to an optical apparatus for irradiating light to an object.

LIST OF REFERENCE SIGNS

100 Oblique Detection System
101 Oblique Detection Optical System
102, 802 One-dimensional Sensor
103 Focused Focal Position
104 Image Focus Position
105, 805 Objective Lens
106, 806 Optical Branching Component
107, 807 Two-dimensional sensor
108 Optical Axis
109, 809 Imaging Lens
120, 350 Moving Unit
200 Inspection Target,
201, 801, 898 Scattered Light
202 Focused Focal Region
203 Defocused Region
204 Normal Line
205 Reference Chip
300, 310, 320 Illumination System
301, 308, 311, 321 Illumination Light
303 Illumination Reshaping Component
305 Wavefront Sensor
306 Incident Wavefront
307 Reflection Wavefront
309 Deformable Mirror
312, 314, 322, 601, 3091 Reflection Component
313 Optical Branching Component/Optical Path Switching Component
323, 331 Optical Path Branching Component/Switching Component
341 Control Component 342 Driving Component
360 Diffraction Light or Scattered Light
370 Illumination Observation System
400 Stage
700 Calculation Processing System
701 Display Device
800 Upward Detection System
901 Illuminated Shape
902 Light Source Model
903 Theoretical Model of Illumination Shaping Component
904 Theoretical Model of Wavefront
1000 Defect Inspection Apparatus
3092 Actuator
3093 Electrostatic Actuator

The invention claimed is:

1. An inspection apparatus comprising:
a wavefront changing unit that reflects light for illuminating a sample, and changes the wavefront of the light; and
an illuminated region forming unit that forms a linear illuminated region on the sample by converging the light reflected by the wavefront changing unit,
wherein the wavefront changing unit includes a reflection plane and a driving section for changing the condition of the reflection plane, and
wherein the wavefront changing unit irradiates light, whose wavefront is optically inverse to a wavefront onto which a factor undesired for inspection is superimposed, onto the illuminated region forming unit.

2. The inspection apparatus according to claim 1,
wherein the optically inverse wavefront is a wavefront having a phase that is the inverse of the phase of the wavefront onto which the factor undesired for the inspection is superimposed.

3. The inspection apparatus according to claim 2,
wherein the width of the illuminated region is equal to or smaller than the width of a focused focal region for the inspection.

4. The inspection apparatus according to claim 3, further comprising:
an oblique detection optical system,
wherein the focused focal region is a region where the focused focal plane of the oblique detection optical system and the surface of the sample intersect with each other.

5. The inspection apparatus according to claim 4, further comprising:
a wavefront sensor that obtains the state of the wavefront of the light reflected by the wavefront changing unit,
wherein the wavefront changing unit changes the wavefront of light entering the illuminated region forming unit into a wavefront with substantially no aberration using information obtained from the wavefront sensor, and
wherein the wavefront changing unit further changes the wavefront with no aberration into the wavefront having a phase that is the inverse of the phase of the wavefront onto which the factor undesired for the inspection is superimposed.

6. The inspection apparatus according to claim 5, further comprising:
a processing unit that creates data used for changing the wavefront with no aberration into the wavefront having the phase that is the inverse of the phase of the wavefront onto which the factor undesired for the inspection is superimposed.

7. The inspection apparatus according to claim 4,
wherein the driving section is disposed at the rear surface of the reflection plane, and includes a plurality of piezoelectric elements that press the rear surface.

8. The inspection apparatus according to claim 4,
wherein the driving section is disposed at the rear surface of the reflection plane, and includes a plurality of electrostatic components that press the rear surface.

9. The inspection apparatus according to claim 4,
wherein the driving section includes a first actuator that performs driving with a first spatial resolution, and a second actuator that performs driving with a second spatial resolution higher than the first spatial resolution.

10. The inspection apparatus according to claim 1,
wherein the illuminated region forming unit forms the illuminated region while changing an elevation angle to the sample, and
wherein the wavefront changing unit changes the wavefront of the light for illuminating the sample in accordance with the change of the elevation angle.

11. The inspection apparatus according to claim 1,
wherein the illuminated region forming unit converges first light and second light onto the substrate at two different elevation angles respectively,
wherein the wavefront of the first light is changed into a first wavefront by the wavefront changing unit, and enters the illuminated region forming unit, and
wherein the wavefront of the second light is changed into a second wavefront by the wavefront changing unit, and enters the illuminated region forming unit.

12. The inspection apparatus according to claim 1,
wherein the wavefront changing unit changes the wavefront of the light in accordance with the height of a pattern on the sample.

13. The inspection apparatus according to claim 1, further comprising:
an environmental measurement unit,
wherein the wavefront changing unit changes the wavefront of the light in accordance with the measurement result measured by the environmental measurement unit.

* * * * *